(12) United States Patent
Friederichs et al.

(10) Patent No.: US 11,865,240 B2
(45) Date of Patent: Jan. 9, 2024

(54) WATER TREATMENT SYSTEMS, DEVICES, AND METHODS FOR FLUID PREPARATION

(71) Applicant: NxStage Medical, Inc., Lawrence, MA (US)

(72) Inventors: Goetz Friederichs, Beverly, MA (US); Dennis M. Treu, Castle Rock, CO (US); Jeffrey H. Burbank, Manchester, MA (US); Yuriy N. Tatashin, Londonderry, NH (US)

(73) Assignee: NxStage Medical, Inc., Lawrence, MA (US)

(*) Notice: Subject to any disclaimer, the term of this patent is extended or adjusted under 35 U.S.C. 154(b) by 257 days.

(21) Appl. No.: 17/189,879

(22) Filed: Mar. 2, 2021

(65) Prior Publication Data

US 2021/0178041 A1    Jun. 17, 2021

Related U.S. Application Data

(60) Continuation of application No. 15/924,425, filed on Mar. 19, 2018, now Pat. No. 10,960,121, which is a
(Continued)

(51) Int. Cl.
*A61M 1/16* (2006.01)
*C02F 1/28* (2023.01)
(Continued)

(52) U.S. Cl.
CPC ........ *A61M 1/1656* (2013.01); *A61M 1/1664* (2014.02); *A61M 1/1666* (2014.02);
(Continued)

(58) Field of Classification Search
CPC .................................................. A61M 1/1656
See application file for complete search history.

(56) References Cited

U.S. PATENT DOCUMENTS

| 4,495,067 A | 1/1985 | Klein et al. |
| 5,024,766 A | 6/1991 | Mahmud |

(Continued)

FOREIGN PATENT DOCUMENTS

| EP | 0056855 A2 | 8/1982 |
| WO | 2003078034 A1 | 9/2003 |

OTHER PUBLICATIONS

A Guide to Laboratory Water Purification [online]. Labconco, 2006 [retrieved on Jul. 23, 2015]. Retrieved from the Internet: (URL: http://www.expotechusa.com/catalogs/labconco/pdf/guide_water.pdf).

(Continued)

*Primary Examiner* — Peter Keyworth
(74) *Attorney, Agent, or Firm* — Potomac Law Group, PLLC

(57) ABSTRACT

A method of automatically ensuring against chloramine contamination in purified product water includes supplying input water to the system and purifying the water to generate the purified product water. The purifying includes removing chlorine and chloramine contamination from the water using a carbon filter and supplying chlorine-depleted water to a deionization filter, and deionizing the chlorine-depleted water using said deionization filter. The product water is supplied to a sensor for continuous monitoring of the resistivity of the purified product water by the first sensor, and an alarm is generated indicating possible chloramine breakthrough when the resistivity of the product water falls below a predetermined resistivity level, which is selected to provide a reserve filter capacity before breakthrough would occur. The carbon filter is replaced at least responsively to the alarm to ensure excess capacity of said carbon filter sufficient to prevent chloramine breakthrough in said product water.

13 Claims, 9 Drawing Sheets

Related U.S. Application Data division of application No. 14/762,831, filed as application No. PCT/US2014/013022 on Jan. 24, 2014, now abandoned.

(60) Provisional application No. 61/756,140, filed on Jan. 24, 2013.

(51) Int. Cl.
| | |
|---|---|
| *C02F 1/42* | (2023.01) |
| *C02F 1/00* | (2023.01) |
| *C02F 1/44* | (2023.01) |
| *C02F 103/02* | (2006.01) |
| *C02F 1/32* | (2023.01) |
| *C02F 101/12* | (2006.01) |

(52) U.S. Cl.
CPC ............ *A61M 1/1672* (2014.02); *C02F 1/283* (2013.01); *C02F 1/42* (2013.01); *C02F 1/001* (2013.01); *C02F 1/32* (2013.01); *C02F 1/441* (2013.01); *C02F 2001/427* (2013.01); *C02F 2101/12* (2013.01); *C02F 2103/026* (2013.01); *C02F 2209/003* (2013.01); *C02F 2209/02* (2013.01); *C02F 2209/05* (2013.01); *C02F 2209/29* (2013.01); *C02F 2209/445* (2013.01)

(56) References Cited

U.S. PATENT DOCUMENTS

| | | | |
|---|---|---|---|
| 5,645,734 | A | 7/1997 | Kenley et al. |
| 5,651,893 | A | 7/1997 | Kenley et al. |
| 5,674,390 | A | 10/1997 | Matthews et al. |
| 5,762,782 | A | 6/1998 | Kenley et al. |
| 5,783,072 | A | 7/1998 | Kenley et al. |
| 5,814,212 | A * | 9/1998 | Hsu ............... B01D 17/0202 210/93 |
| 6,258,278 | B1 | 7/2001 | Tonelli et al. |
| 6,562,205 | B1 | 5/2003 | Ban et al. |
| 6,745,903 | B2 | 6/2004 | Grandics |
| 7,189,314 | B1 | 3/2007 | Pace et al. |
| 2006/0011546 | A1 | 1/2006 | Livingston |
| 2007/0007208 | A1 * | 1/2007 | Brugger ............... A61M 1/166 210/645 |
| 2008/0230450 | A1 | 9/2008 | Burbank et al. |
| 2008/0296208 | A1 | 12/2008 | Ikeyama et al. |
| 2009/0045121 | A1 | 2/2009 | Kabayama et al. |
| 2009/0182263 | A1 | 7/2009 | Burbank et al. |
| 2010/0051552 | A1 * | 3/2010 | Rohde ............... A61M 1/287 210/644 |
| 2011/0300230 | A1 | 12/2011 | Peterson et al. |
| 2012/0216605 | A1 | 8/2012 | Silveri |
| 2012/0325696 | A1 | 12/2012 | Burbank et al. |
| 2013/0126430 | A1 | 5/2013 | Kenley et al. |

OTHER PUBLICATIONS

Ahmad, Suhail, "Essentials of water treatment in hemodialysis," Hemodialysis International, Apr. 2005, 9(2): pp. 127-134.

Chloramines [online]. Environmental Protection Agency, Guidance Manual, Chapter 6, Apr. 1999 [retrieved on Jul. 23, 2015]. Retrieved from the Internet (URL: http://water.epa.gov/lawsregs/rulesregs/sdwa/mdbp/upload/2001_01_12_mdbp_alter_chapt_6.pdf).

European Best Practice Guidelines on Haemodialysis, "Section IV: Dialysis Fluid Purity" Nephrology Dialysis Transplantation, Jul. 2002, 17(suppl. 7): pp. 45-62.

Examination Report dated Jun. 1, 2016 for Application No. GB1514184.9.

Examination Report for European Patent Application No. 14742933.6 dated Jul. 20, 2017.

Examination Report, dated Sep. 28, 2015, in UK Application No. GB1514184.9.

Extended European Search Report dated Aug. 12, 2016 for European Patent Application No. 14742933.6.

Hemodialysis, Application Bulletin [online]. Myron L. Company, May 2012 [retrieved on Jul. 23, 2015]. Retrieved from the Internet (URL: http://www.myronl.com/PDF/application_bulletins/hemoab.pdf).

International Search Report and Written Opinion for International Application No. PCT/US14/13022, dated Jul. 11, 2014.

Monitoring your Dialysis Water Treatment System [online]. Northwest Renal Network, Jun. 2005 [retrieved on Jul. 23, 2015]. Retrieved from the Internet (URL:www.nwrenalnetwork.org/watermanual.pdf).

Perez-Garcia et al., "Chloramine, a sneaky contaminant of dialysate," Nephrology Dialysis Transplantion, 1999, 14(11): pp. 2579-2582.

Reverse Osmosis Technical Data [online]. Vagabond Water, 2008 [retrieved on Jul. 23, 2015]. Retrieved from the Internet (URL: http://web.archive.org/web/20081229100844/http://www.vagabondwater.com/graphics/File/REVERSE_OSMOSIS_TECHNICAL_DATA.pdf).

Search Report dated Jun. 1, 2016 for Application No. GB1514184.9.

Water Treatment System for Dialysis [online]. Advanced Water Technology, Peter Taboada, 2011 [retrieved on Jul. 23, 2015]. Retrieved from the Internet (URL: http://web.archive.org/web/20110601000000*/http://www.fulgormarine.com/download/petertobata/WATER%20TREATMENT%20SYSTEM%20FOR%20DIALYSIS%20_DOSSIER_%20rev2.pdf).

\* cited by examiner

WATER TREATMENT SYSTEMS, DEVICES, AND METHODS FOR FLUID PREPARATION

CROSS-REFERENCE TO RELATED APPLICATIONS

The present application is a continuation of U.S. patent application Ser. No. 15/924,425 filed Mar. 19, 2018, which is divisional of U.S. patent application Ser. No. 14/762,831 filed Jul. 23, 2015, which is a U.S. national stage entry of International Application No. PCT/US2014/13022 filed Jan. 24, 2014, which claims the benefit of U.S. Provisional Application No. 61/756,140 filed on Jan. 24, 2013, all of which are incorporated herein by reference in their entirety.

BACKGROUND

Many medical applications require purified water for purposes of preparing treatment fluids, for example, hemofiltration, tissue irrigation, dialysis. High purity water is also used in the electronics industry and pharmaceutical industry. To remove contaminants from water, so as to generate high purity water, filtration systems may be used. To supply high purity water for medical processes where treatment is performed at a treatment location, a filtration system may be provided at the same location. To supply high purity water for medical processes where treatment is performed at a treatment location, high purity water may be generated at a plant, stored in containers, and shipped to the treatment location.

Water is a source of risk for patients receiving hemodialysis. Risk of imperfections in water treatment and testing can affect one or multiple patients tied to a single treatment plant. Failure to recognize water containing chemical, bacteria, or toxin contamination poses a serious and persistent concern for hemodialysis patients. Chloramine is a particularly difficult problem because it is toxic and hard to detect. In dialysis systems, chloramine must be removed from dialysate to prevent it from entering the bloodstream across the dialyzer membrane. In hemofiltration, replacement fluid containing chloramine at even lower levels can cause harm by directly convecting chloramine into the blood.

In deionization systems, water quality may be monitored by measuring resistivity because the conductivity is too low to measure accurately. The acceptable limit of resistivity is greater than 1 megohm-cm resistance. Safeguarding against residual chloramine in reverse osmosis (RO) and deionization (DI) systems relies on a different system from mere resistance testing. Activated carbon is used for chloramine removal. Large volumes of carbon may be required. Water purification for dialysis typically uses granular activated carbon. These carbon filtration plants may have multiple stages, typically two stages. Chloramine breakthrough may be monitored by regular manual testing for chloramine after the first stage so that the second stage can serve as a back-up and provide a safety margin between chloramine tests. In known systems, a backup carbon filter with strip testing is the standard. Two carbon stages are provided. When the first stage is exhausted, as indicated by strip testing between the two stages, the first stage filter unit is replaced by the filter unit previously used as the second stage and a new filter is placed in the second stage position. The testing and filter replacement represent risks because mistakes can be made, particularly when the procedure of placing the correct filters in position. Proper testing is required to ensure the system is properly set up and maintained. It would be desirable to have a simpler system that provides a high level of security against chloramine transmission to product water to ensure patient safety without the risk of a complex maintenance procedure.

SUMMARY

In a water purification plant that supplies pure water to a dialysate preparation system, water may be purified continuously. For safety it is desirable for water purification systems to provide automatic detection of conditions that could pose a safety risk. For example, the current safe method of detecting chloramine in high purity water employs a manual test, for example using chloramine test strips. In embodiments of the disclosed subject matter, chloramine breakthrough and/or determination of predefined levels of chloramine in purified water is provided by a deionization plant in which water resistivity is increased to a level substantially above 1.0 megohm-cm or higher. For example, in embodiments, sufficient deionization capacity in a filtration plant is provided to bring the level of resistivity of the product water above 10 megohm-cm. According to the embodiments, the product water resistivity is monitored continuously and compared to a calibration curve to indicate the level of chloramine in the product water.

The purification of water for medical treatment purposes to levels of resistivity above 2.5 megohm-cm is conventionally not done. Rather, the level of 2.5 megohm-cm is generally considered sufficient to indicate medically adequate levels of purity. However, at levels of resistivity of 2.5 megohm-cm, undesirable levels of chloramine are difficult to detect based on resistivity measurements because the signal resulting from the presence of chloramine is essentially buried in the background resistivity signal. This is why chloramine detection in medical treatment fluid preparation plants is performed by other tests such as manual strip tests.

According to the embodiments of the disclosed subject matter, product water is purified to a level of resistivity that is high enough to allow the chloramine concentrations that are at clinically relevant levels to be indicated by resistivity measurement. It has been confirmed by experiment that the levels of chloramine can be reliably predicted, responsively to resistivity, using a calibration curve in which chloramine is calibrated against resistivity. For the calibration, high resistivity water (e.g., 10 megohm-cm water) provides a baseline, a measured resistivity above which, it has been determined, is sufficient for the chloramine signal to be reliably detected. In other words, if the background resistivity is lowered sufficiently, the chloramine resistivity can be detected with sufficient reliability for use in preparing medicaments for blood treatment.

In embodiments, a water purification plant is capable of reducing the levels of ions in water to a level sufficient to indicate the presence, or absence, of chloramine in the water based on a resistivity measurement. The purification plant may be configured such that the resistivity of the water, in the absence of chloramine, is greater than 2.5 megohm-cm. In further embodiments, the level of ions is reduced to a level where the water resistivity is at least 5 megohm-cm. In still further embodiments, the level of ions is reduced to a level where the water resistivity is at least 10 megohm-cm. Any of these levels may be provided in a data store to compare to the resistivity signal from a resistivity sensor. Alternatively, an equivalent parameter that may be compared to the signal from a resistivity sensor may be stored, for example, a predefined current or voltage generated by the resistivity sensor and indicative of resistivity.

In embodiments, the water treatment plant upstream of the chloramine removal stage may be configured such that its predicted ability to remove solutes, other than chloramine, is substantially higher than necessary to produce product water that has a resistivity higher than the predefined level (e.g., 2.5, 5, or 10 megohm-cm, for example) in the absence of chloramine. The water treatment plant may be provided with a chloramine removal stage whose exhaustion is to be monitored. The chloramine removal stage may be attached to the water treatment plant to receive product water from the water treatment plant. Given the predicted excess capacity of the water treatment plant, the indicated resistivity may be attributed to chloramine level and used as a basis for maintaining a chloramine removal stage. For example, the chloramine stage may be replaced when the chloramine level rises to a level indicating the chloramine removal stage is exhausted. For example, in embodiments, the chloramine removal stage includes a bed of activated carbon granules or "carbon bed."

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DETAILED DESCRIPTION

Figure 1A:
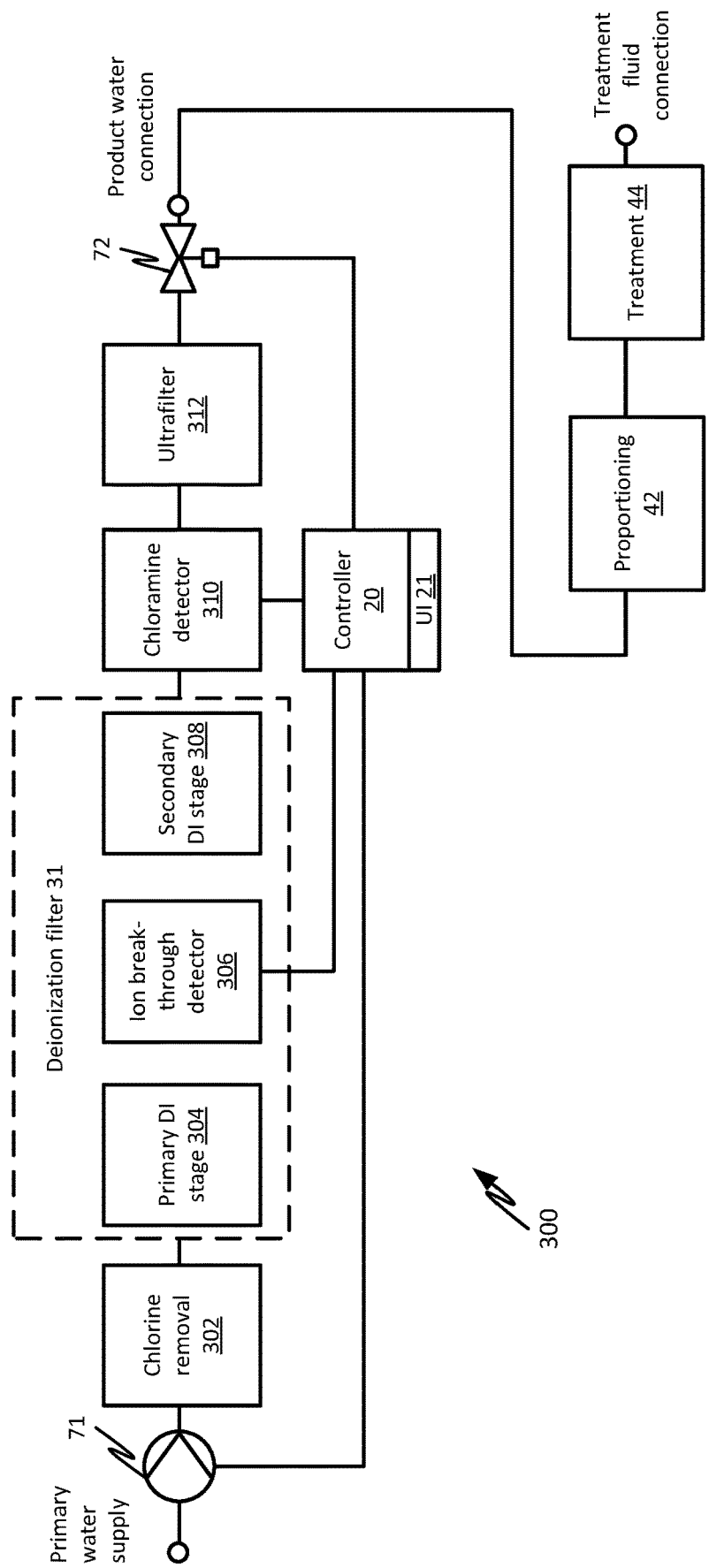
FIG. 1A shows a water purification system configured to provide substantially chloramine free product water in which deionization filter breakthrough and chloramine levels are detected automatically and which employ one or more chloramine removal stages such as a carbon bed and a deionization filter that increases the product water resistivity to a point that allows chloramine to be detected in product water, according to embodiments of the disclosed subject matter.

Referring to FIG. 1A, a water purification plant 300 with optional proportioning and medical treatment components is illustrated. Water from a primary water supply is pumped by a pump 71 controlled by a controller 20. The controller 20 has a user interface 21 adapted for indicating various alarm conditions including the detection of breakthrough of ionic species and detection of chloramine levels exceeding a desired level. A chlorine removal filter 302 is configured for removing chlorine and chloramine. Chlorine removal filter 302 may be, for example, an activated carbon filter or any of the embodiments of a chlorine or chloramine filter identified hereinbelow. Water then flows through a deionization filter 31 that is adapted to reduce a level of ionic species in the product water emerging therefrom to a high resistivity that permits chloramine to be detected by a chloramine detector 310. Chloramine detector 310 indicates a level of chloramine by detecting resistivity and temperature and providing a signal indicating such to the controller 20. The controller may calculate the level of chloramine by using a predefined calibration curve which compensates a resistivity signal to account for the effect of temperature to yield a level of chloramine or other residual ionic species in the product water flowing through the chloramine detector. An ultrafilter 312 may be provided to ensure sterile water is provided at the product water connection for uptake by a proportioning system 42 for creating medicament for a treatment device 44. The latter two elements may or may not be present in the system and may only show a suitable use for the chloramine free product water.

In any of the disclosed embodiments, chloramine may be detected using data that relates resistivity to chloramine level (or, equivalently, concentration thereof) or data that relates resistivity and temperature to chloramine level (or, as stated, equivalently, concentration thereof). The data that relates chloramine levels to these parameters may be obtained using a calibration technique in which the parameter is measured in water containing various levels of chloramine (for resistivity-chloramine level data) or various levels of chloramine at various temperatures (for resistivity, temperature-chloramine level data).

The deionization stage 31 includes an ion breakthrough detector 306 which may, like the chloramine detector 310, include temperature and resistivity sensors to allow the controller to generate a level estimation for dissolved ionic species. The level estimation may be used by the controller to generate a first alarm signal which may be used to output an indication that the primary deionization stage 304, and possibly the secondary deionization stage 308, should be replaced. The pump 71 and valve 72 may be controlled in response to the level estimation and/or the calculated level of chloramine provided by the chloramine detector 310. For example, out of bounds indications for ionic species and/or chloramine may trigger control by the controller 20 of the flow, for example, the flow may be halted or diverted to prevent the use of the product water that is unsafe.

Figure 1B:
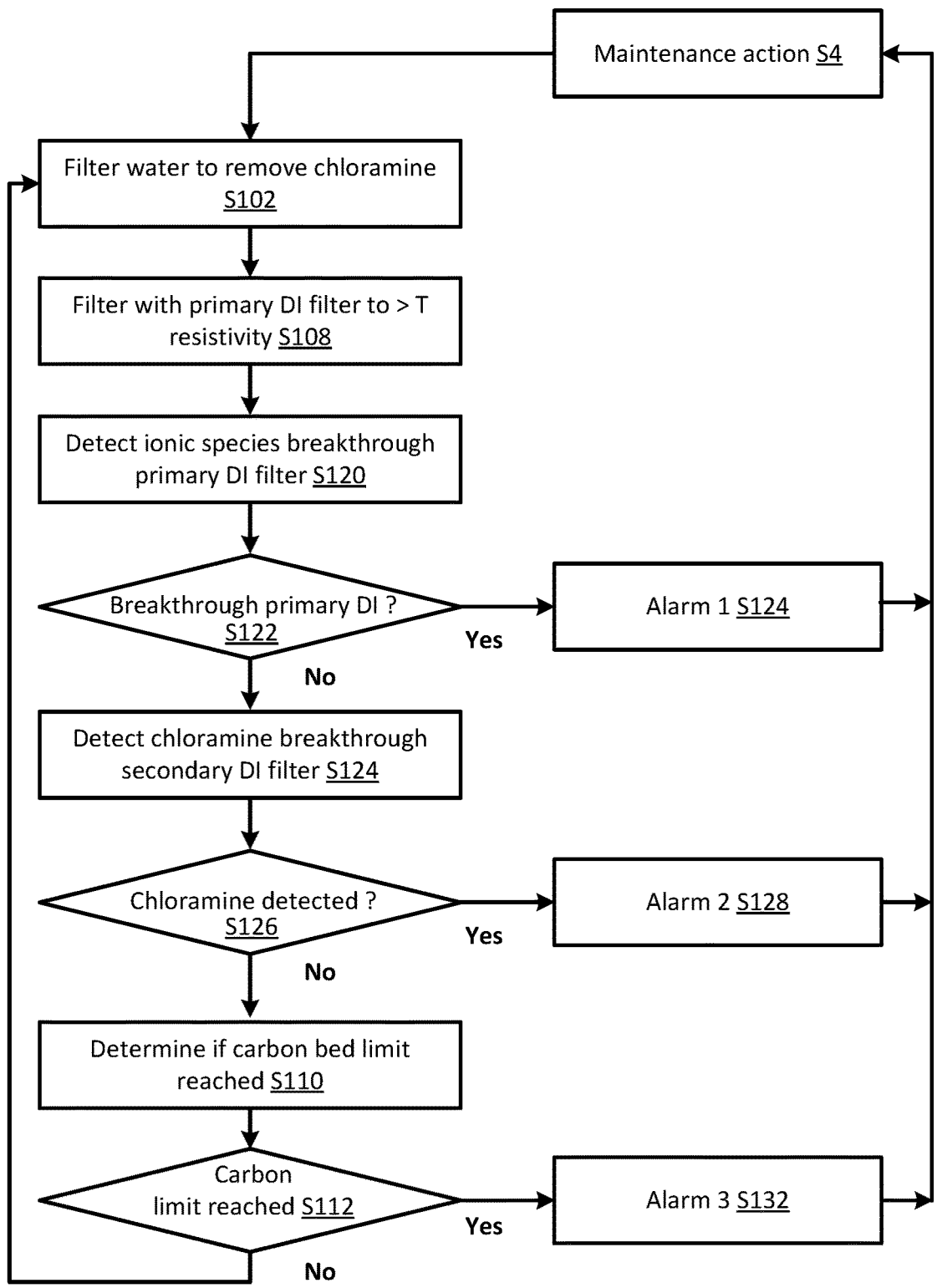
FIG. 1B shows a method of purifying water for use, for example, in the embodiment of FIG. 1A and other embodiments described below.

FIG. 1B shows a method of purifying water for use in an application requiring water having a predetermined level of chloramine therein. In step S102, water is filtered to remove chloramine, for example, by passing through an activated carbon filter (also simply called carbon filter or carbon bed). The chloramine level in the water emerging from the filter in step S102 is reduced to a level such that product water has a predefined "safe" level. In step S108, a primary deionization filter is used to reduce dissolved species to a level such that later on, chloramine at a predefined level can be detected. Although here, and elsewhere in the instant specification, reference is made to resistivity being the indicator of chloramine level, it should be kept in mind that resistivity may be compensated by temperature, and the chloramine level may be indicated by a combination of resistivity and temperature rather than resistivity alone.

In step S120, a resistivity (or resistivity+temperature) sensor is used to detect any breakthrough of ionic species from the primary stage deionization filter. At S122, it is determined if the level of ionic species rises above a threshold stored by the controller thereby indicating breakthrough of the primary stage deionization filter. Failure of the primary deionization stage is indicated at S124 by the generation of a first alarm signal. The alarm signal may be used by the controller to generate an informative display indicating that the primary deionization filter has failed or that it needs to be replaced. The failure of the primary filter is typically from exhaustion and may be replaced in response to the first alarm signal output. The first alarm signal generated as S124 may be internal to the controller and used to control the fluid circuit of a water purification plant, for example, to redirect product water to a waste receptacle or drain or to prevent product water from flowing from it until appropriate maintenance (S104) is done and a condition reset is generated by an operator.

At S123, chloramine is detected in water emerging from the secondary deionization filter. At S126, it is determined if the level of chloramine exceeds a safe threshold stored by the controller. Detection of unsafe levels of chloramine (or other conditions related to effectiveness of chloramine removal, such as detection of increasing levels of chloramine in the product water even if such levels are currently below the safe threshold) results in a second alarm signal being generated at S128. The second alarm signal generated as S128 may be internal to the controller and used to control the fluid circuit of a water purification plant, for example, to redirect product water to a waste receptacle or drain or to prevent flow of product water from the system until appropriate maintenance (S104) is done and a condition reset is generated by an operator. In this case, appropriate maintenance may include having the operator replace the chloramine removal filter or carbon filter.

At step S110, it is determined if a chloramine removal filter, such as carbon, has reached a time-of-use or water volume-processed limit (or some other limit). This determination may be made by a controller, such as controller 20 of FIG. 1A, by comparing measured cumulative time and/or volume and comparing the measurement to a stored predefined value. If the limit is reached as determined in S112, a third alarm signal at S132 is generated. In response to the third alarm signal, which may be internal to the controller and used to control the fluid circuit of a water purification plant, for example, to redirect product water to a waste receptacle or drain or to prevent product water from flowing from it until appropriate maintenance (S104) is done. In this case, appropriate maintenance may include having the operator replace the chloramine removal filter or carbon filter. If alarms are not generated, control returns to S102.

Figure 2A:
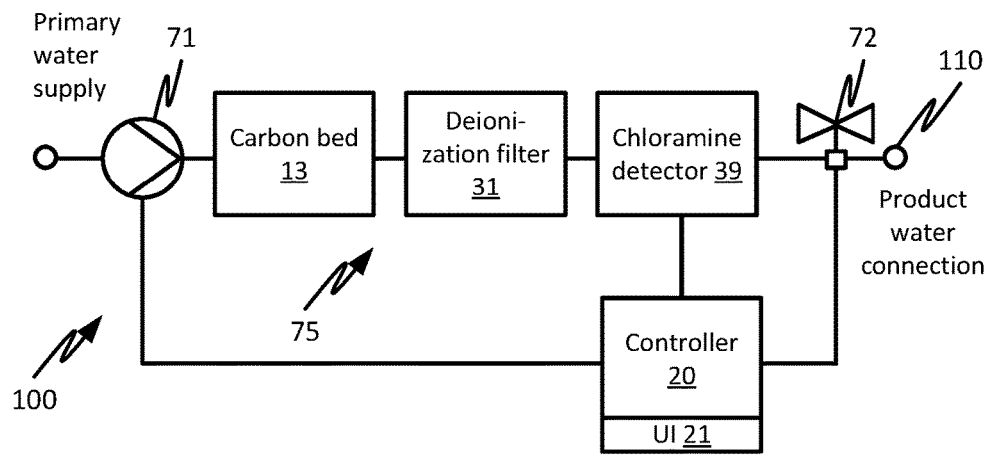
FIG. 2A shows a water purification system configured to provide substantially chloramine free product water in which chloramine levels are detected automatically and which employ one or more chloramine removal stages such as a carbon bed and a deionization filter that increases the product water resistivity to a point that allows chloramine to be detected in product water when and if chloramine breaks through the filtration elements, according to embodiments of the disclosed subject matter.

FIG. 2A shows a water purification system 100 that provides substantially chloramine free product water to a product water connection 100 for use in any application. Chloramine levels are tested automatically at a chloramine detector 39. One or more chloramine removal stages, identified in the drawing as a carbon bed 13 but which may be any suitable filter that removes chloramine including ultraviolet combined with one or more other filter elements which may include carbon. A deionization filter 31 is configured to increase the resistivity to a level that permits chloramine to be detected in the water deionized by it. In embodiments, the resistivity is increased to a level above 2.5 megohm-cm. According to further embodiments, the resistivity is increased to a level above 4 megohm-cm. According to further embodiments, the resistivity is increased to a level above 6 megohm-cm. According to further embodiments, the resistivity is increased to a level above 8 megohm-cm.

According to further embodiments, the resistivity is increased to a level of at least 10 megohm-cm.

In embodiments, the water provided at product water connection 110 is provided at medical treatment facilities or at a home treatment facility for use in blood treatment where extremely low levels of chloramine are required. In such applications, although chloramine at potentially unsafe levels is not feasible to detect based on at product water resistivity levels normally required for such medical treatments, it has been found that if the water is purified to achieve resistivity beyond the levels required for blood treatment, unsafe levels of chloramine can be detected based on resistivity. Thus, according to embodiments, the carbon bed 13 is chosen to reduce chloramine to safe levels for blood treatment. The deionization filter 31 is chosen to provide filtered water therefrom whose resistivity is above the level required for safe blood treatment, for example, 10 megohm-cm. As the system is used to generate product water, when a resistivity is detected that is below a predetermined level, for example 5 megohm-cm, the system determines that an unsafe chloramine level is responsible (or some other error condition exists) and a controller 20 that receives signals from the chloramine detector 39, takes some step such as outputting an indication to an operator (using a connected user interface 21, for example) and/or shutting the system down by deactivating a pump 71 or operating a control valve 72 to halt or divert the flow of unsafe product water.

In embodiments, a chloramine level can be determined based on the measured resistivity and temperature of the product water. The determined chloramine level can then be compared to a threshold in determining whether to activate an alarm, for example, where chloramine levels exceed a predetermined safe threshold rate. Alternatively or additionally, a rate of change of chloramine levels can be used as the basis for triggering an alarm, for example, when increasing chloramine levels that are still less than the safe threshold may be indicative of imminent failure of one or more filter components that may subsequently result in unsafe chloramine levels.

User interface 21 may include one or more conventional mechanisms to allow a user to input information to and interact with the control system to control the system 100 or any of the other systems described herein or variations thereof disclosed herein. Such mechanisms may include a keyboard, wireless receiver such as a Bluetooth connection, a display, a mouse, a pen, touchscreen, voice recognition module, touchpad, buttons, speakers, alarm lights, printer, cellular phone, etc., for example.

Controller 20 may include a microprocessor, a programmable microcomputer, memory, non-volatile storage such as rotating medium or solid state drive, an interface to a server-based or remote application computer running software that provides control commands (for example, a cloud-based control), etc., for example.

Deionization filter 31 may include any of a variety of deionization filters including separate strong acid cation and strong base anion filters, a mixed bed filter, or any other suitable deionization filter.

Carbon bed 13 may be replaced by alternative chloramine filter devices as mentioned, including UV treatment in combination with RO or other mechanisms for reducing chloramine content.

Pump 71 may be any type of pump and may be present or not to form alternative embodiments. The pump 71 may be located in different positions in the fluid circuit 75 to move water or fluid therethrough.

Control valve 72 may halt or divert flow. For example, it may be adapted to divert water to a drain (not shown) in the event unsafe or uncertain water properties are detected responsively to the chloramine detector 39 and based on a control signal from the controller 20. The control valve 72 may also be positioned at other locations in the fluid circuit 75.

Chloramine detector 39 may be a resistivity cell or equivalent device which relies on electrode contacts or non-contact induction elements for measuring resistance or impedance in a flow channel or vessel. In embodiments, the chloramine detector 39 permits continuous flow therethrough while it continuously or periodically generates a signal indicating a current resistance in a flow channel or vessel therein. The chloramine detector may also include a temperature sensor such as a thermistor, a thermocouple, resistance temperature detectors (RTD), quartz oscillators, bimetallic strips, bulb thermometers, etc. The temperature sensor may be an active temperature sensor that is adapted to generate a net-zero heat flux between the measured liquid and the temperature sensor by active cancelation using a thermal source. In embodiments with a temperature sensor, the chloramine detector 39 may convey temperature and resistance or resistivity data or signal to the controller 20 or it may perform a temperature compensation and transmit a signal corresponding to parts per million PPM of dissolved solids. Alternatively, the temperature sensor may be embodied as a separate component and provided adjacent to the chloramine detector 39, or upstream or downstream therefrom, so as to provide a measure of the temperature of the product water interrogated by the chloramine detector 39.

Figure 2B:
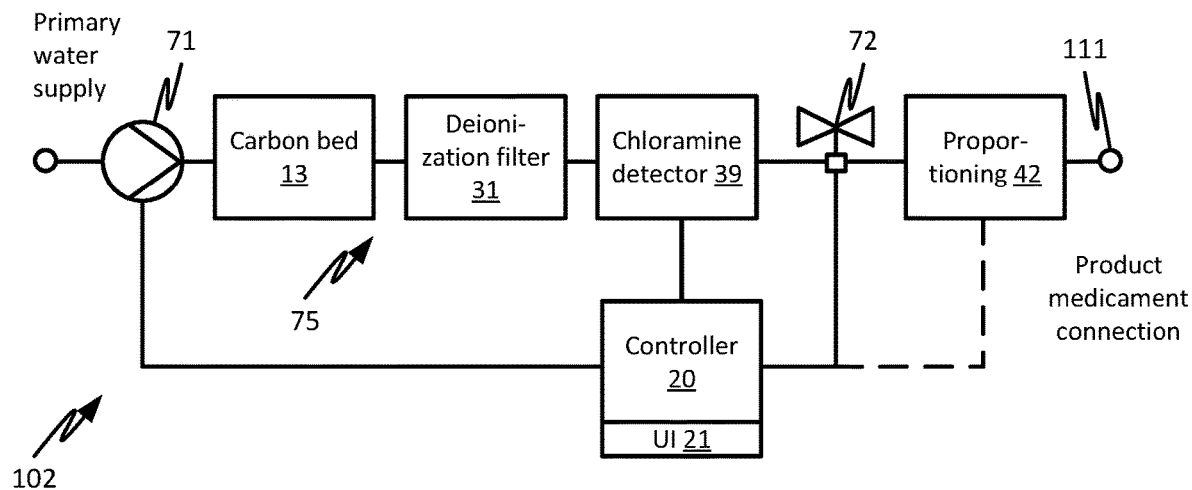
FIG. 2B shows a medicament preparation system configured to provide substantially chloramine free product water to a proportioning system which in turn provides medicament for consumption on demand and in which chloramine levels are tested automatically and which employ one or more chloramine removal stages such as a carbon bed and a deionization filter that increases the product water resistivity to a point that allows chloramine to be detected in product water when and if chloramine breaks through the filtration elements, according to embodiments of the disclosed subject matter.

FIG. 2B shows a medicament preparation system 102 providing substantially chloramine free product water to a proportioning system which in turn provides medicament for consumption on demand and in which chloramine levels are tested automatically and which employ one or more chloramine removal stages such as a carbon bed and a deionization filter that increases the product water resistivity to a point that allows chloramine to be detected when and if chloramine breaks through the filtration elements, according to embodiments of the disclosed subject matter. The embodiment of FIG. 2B is substantially the same as that of FIG. 2A with all the variations identified therewith, except that it adds a downstream proportioning element 42 adapted for preparing a medicament from the product water. The proportioning element 42 may include its own one or more controllers, pumps, valves, user interface, etc. The proportioning element 42 may output control signals to controller 20 to apply a command indicating a demand for purified product water. The controller 20 may be configured to operate the pump 71 and other systems to provide product water. In alternative embodiments, the proportioning element 42 may provide a mechanical signal such as by running a pump so as to create a vacuum or reduced pressure that is detected by a pressure sensor (not shown) upstream thereof so that the controller 20 on detecting the demand indicated by the reduced pressure, operates the pump 71 to deliver product water. Medicament may be generated by diluting concentrates or dissolving powders (or a combination) in controlled fashion to permit the extraction of prepared medicament from medicament connector 111.

Figure 2C:
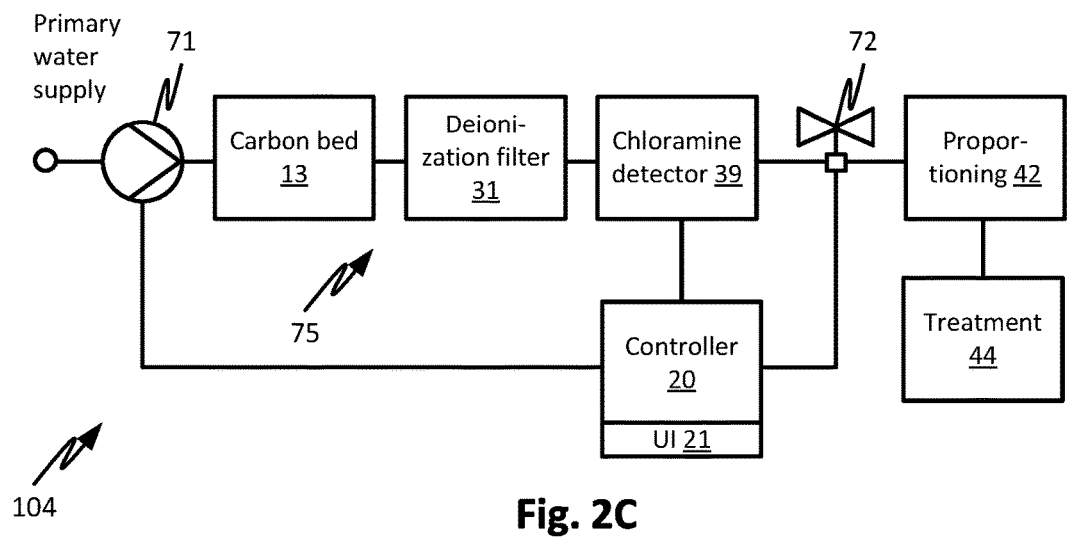
FIG. 2C shows a medical treatment system configured to provide substantially chloramine free product water to a proportioning system which in turn provides medicament for consumption on demand by a medical treatment device and in which chloramine levels are tested automatically and which employ one or more chloramine removal stages such as a carbon bed and a deionization filter that increases the product water resistivity to a point that allows chloramine to be detected in product water when and if chloramine breaks through the filtration elements, according to embodiments of the disclosed subject matter.

FIG. 2C shows a medical treatment system 104 providing substantially chloramine free product water to a proportioning system which in turn provides medicament for consumption on demand by a medical treatment device and in which chloramine levels are tested automatically and which employ one or more chloramine removal stages such as a carbon bed and a deionization filter that increases the product water resistivity to a point that allows chloramine to be detected when and if chloramine breaks through the filtration elements according to embodiments of the disclosed subject matter. The embodiment of FIG. 2C is substantially the same as that of FIG. 2B with all the variations identified therewith, except that it adds a downstream treatment element 44 adapted for performing a medical treatment using the product medicament from the product water. In embodiments, the treatment element is a blood treatment device, for example, a hemofiltration system, a hemodialysis system, a peritoneal dialysis system, or a hemodiafiltration system. The treatment element 44 may be connected to apply commands to the proportioning element 42 and/or the controller 20 to provide for on-demand supply of medicament. The treatment element 44 may include its own one or more controllers, pumps, valves, user interface, etc. The controller 20 may be configured to operate the pump 71 and other systems to provide product water responsively to commands from the treatment element 44. In alternative embodiments, the treatment element 44 may provide a mechanical signal such as by running a pump so as to create a vacuum or reduced pressure that is detected by a pressure sensor (not shown) upstream thereof so that the proportioning element 42 or the controller 20 on detecting the demand indicated by the reduced pressure, operate accordingly to deliver product medicament to the treatment element 44.

Figure 2D:
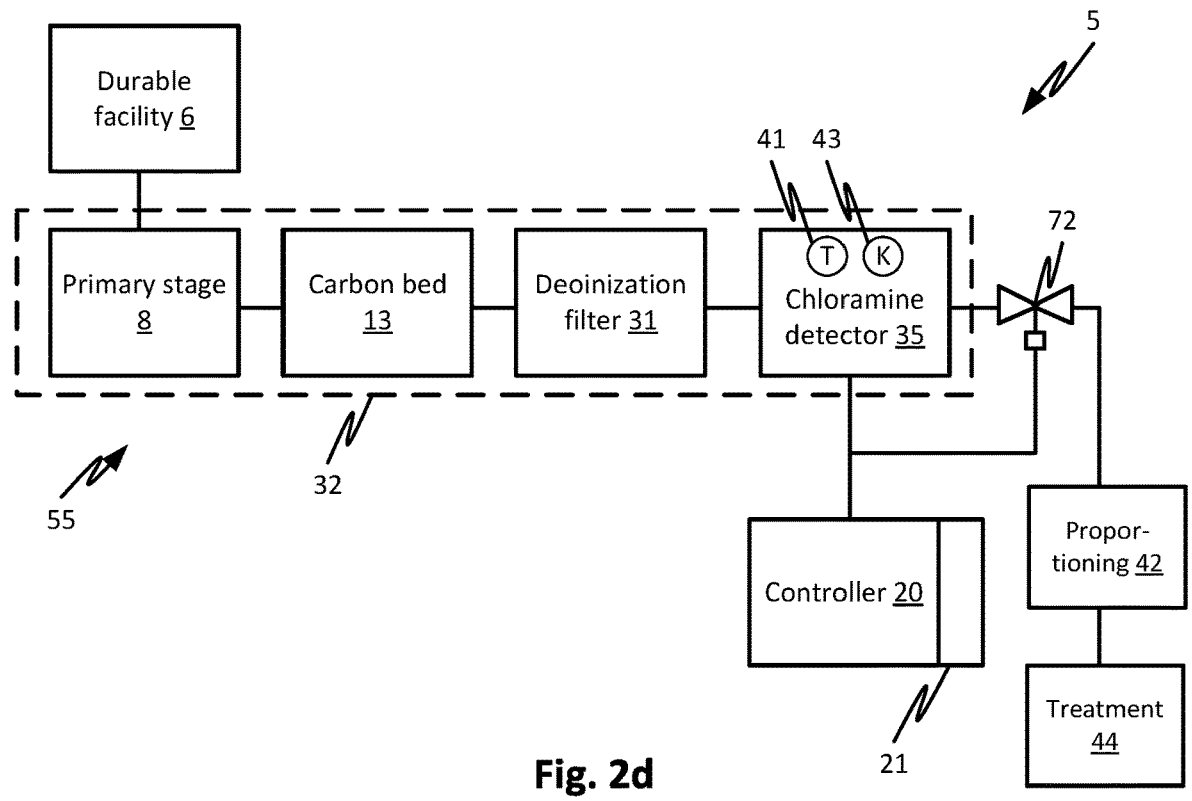
FIG. 2D shows an embodiment consistent with that of FIG. 2C and in connection with which, various embodiments consistent with those of FIGS. 2A and 2B are also described, according to embodiments of the disclosed subject matter.

FIG. 2D shows an embodiment consistent with that of FIG. 2C and in connection with which, various embodiments consistent with those of FIGS. 2A and 2B are also described according to embodiments of the disclosed subject matter. A blood treatment device 5 includes a water purification element 55 which includes a durable facility 6, a primary stage 8, a carbon bed 13, a deionization filter 31, a chloramine detector 35, and a controller 20 with user interface 21. Durable facility 6 may include a pump, flow sensor, backflow preventer, a valve, UV water treatment, a temperature and/or pressure sensor, and/or other elements for primary treatment and/or flow management. The durable facility 6 may be connected to the controller for control of a pump and/or valve and to receive signals from sensors therein. Carbon bed 13 and deionization filter 21 may be as described above including the variations thereof. See discussion of FIG. 2A embodiments. Chloramine detector 35 may be as described with reference to chloramine detector 39 described above including the variations thereof. In the present drawing, temperature and resistance measuring elements 41 and 43 are figuratively indicated although the chloramine detector 35, may include only resistance measuring element as discussed with reference to FIG. 2C. Valve 72, proportioning element 42 and treatment element 44 may be as described in reference to FIGS. 2B and/or 2C including the variations, particularly including the control inputs to the controller 20.

A resistivity detector 35 may incorporate at least one of any type of resistivity sensor 42 of sufficient sensitivity to measure at least a resistivity of 10 megohm-cm. The resistivity sensor or sensors 43 may be of a contact type with electrodes that are wetted by the product water or non-contact sensors such as induction coils. Preferably, at least one temperature sensor 41 is also provided to measure the temperature of the water in the path along which the resistivity is measured. The combination of the temperature 41 and resistivity 43 sensors is identified as the resistivity detector and may be advantageously combined in a single device, component, or portion of the water treatment system 5.

In embodiments, the primary stage 8, carbon bed 13, deionization filter 31, and chloramine detector 35 form a perishable unit 32 which is replaced as a unit when water of unsuitable quality is detected by the chloramine detector 35 or when the controller predicts that one or more of the elements thereof is exhausted. See discussion of FIG. 3 which may relate to the maintenance and control of any and all embodiments. In further embodiments, the primary stage 8 is separate from the perishable unit 32 and may be integrated in the durable facility 6. In further embodiments, one or both of the chloramine detector 35 and primary stage 8 is/are separate from the perishable unit 32. In any embodiment, the deionization filter 31 may include any of a variety of deionization filters including separate strong acid cation and strong base anion filters, a mixed bed filter, or any other suitable deionization filter.

Primary stage 8 may be a filtration stage that provides a plurality of stages of filtering including deionization or reverse osmosis filtering. The downstream stages to which water filtered by primary stage 8 is provided may thus have the primary function of removing chloramine.

Figure 3:
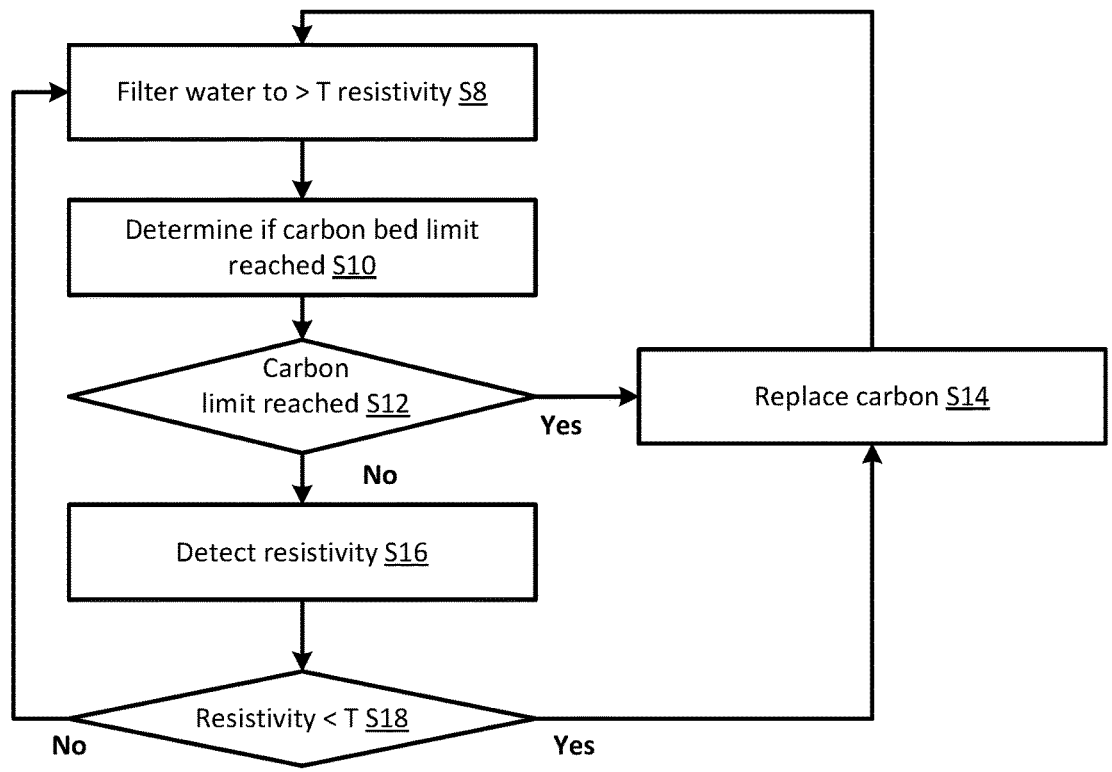
FIG. 3 shows a flow chart for providing purified product water, according to embodiments of the disclosed subject matter.

Referring now to FIG. 3, in any of the embodiments disclosed herein, at S8, water is filtered to a level of purity where its resistivity is greater than some predefined level T which may be detected and confirmed by a chloramine detector. In embodiments T is greater than a minimum requirement for a treatment. In embodiments, T is 2.5, 4, 6, 8, or 10 or more megohm-cm. Alternatively or additionally, a level of impurity may be in parts per million (PPM) or other similar units rather than resistivity but may be detected via detecting resistance of fluid in a cell. The level of impurity may be generated by temperature compensation of a resistance measurement in a cell of known configuration as is known. Thus filtration to a certain resistivity may be a de facto requirement resulting from an impurity concentration which is established as the design requirement for the filtration of water. For example, the resistivity and temperature of product water may be measured and used to determine a chloramine rate in the product water.

At step S10, it is determined if a chloramine removal filter such as carbon has reached a time-of-use or water volume-processed limit (or some other limit). This determination may be made by a controller such as controller 20 by comparing measured cumulative time and/or volume and comparing the measurement to a stored predefined value. If the limit is reached as determined in S12, the chloramine removal filter or carbon filter is replaced in step S14 and monitoring continues at S8. In S16, resistivity or concentration (e.g., chloramine rate in the product water) is detected which is effective for revealing chloramine levels due to the resistivity of the product water being below T. If the resistivity is less than T or if the chloramine rate as determined from the measured resistivity and temperature is equal to or greater than a safe threshold, the chloramine removal filter or carbon filter is replaced in step S14 and monitoring continues at S8. If resistivity fails to indicate chloramine in the product water, or if the chloramine rate as determined from the measured resistivity and temperature is less than the safe threshold, then monitoring continues at S8.

In any of the embodiments, instead of measuring resistivity of product water directly, it is possible to concentrate solutes, including chloramine, in the product water using reverse osmosis and measuring the resistivity of the product water to calculate whether the level of resistivity in the product water itself is over a predetermined limit. This inferential technique may be employed in any of the embodiments.

Figure 4:
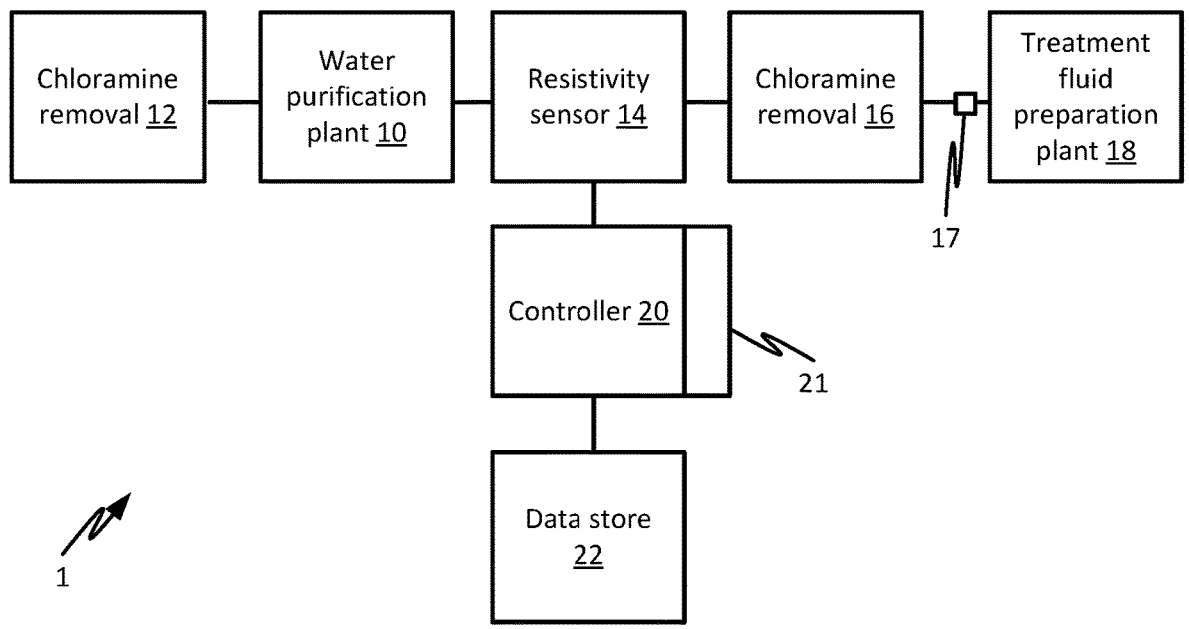
FIG. 4 shows a diagram of a water purification system in which chloramine levels are tested automatically and in which fixed or replacement components include chloramine removal stages, according to embodiments of the disclosed subject matter.

Referring to FIG. 4, a water purification system 1 has a water purification plant 10 which filters water from a chloramine removal stage 12. Chloramine removal stage 12 removes chloramine from water while water purification plant 10 further filters the water to remove other particles. The filtered water is conveyed through a resistivity sensor 14 and then to a further chloramine removal stage 16 from which product water is provided. FIG. 4 shows an example embodiment in which product water is fed to a treatment fluid preparation plant 18 which may combine the product water with other materials to create a treatment fluid such as dialysate. In alternative embodiments, the product water is supplied directly to a port 17 from which it can be transferred for other uses on demand or continuously to a plant in which the water is stored in containers.

A controller 20, for example a programmable controller, is configured to access a data store 22 with data that stores one or more predefined resistivity levels. The controller 20 is configured to compare a signal from the resistivity sensor 14, indicative of the resistivity of the water output from the water purification plant 10, to the predefined resistivity and responsively output an indication on an output device 21. Output device 21 may be, for example, a digital display, a cellular transceiver, a network transceiver that generates updates to a web page for consultation by an operator, an audio transducer, or an output that sends digital messages to a downstream device that receives purified water. The controller 20 may be further configured to calculate a predicted time until exhaustion of the chloramine removal stage 12 and to output display information responsive to the predicted time until exhaustion. For example, the display may indicate a number of days until exhaustion and provide a visual control to allow a user to display instructions for performing a maintenance operation that will refresh the ability of the chloramine removal stage 12 to remove chloramine to a safe level.

Figure 5:
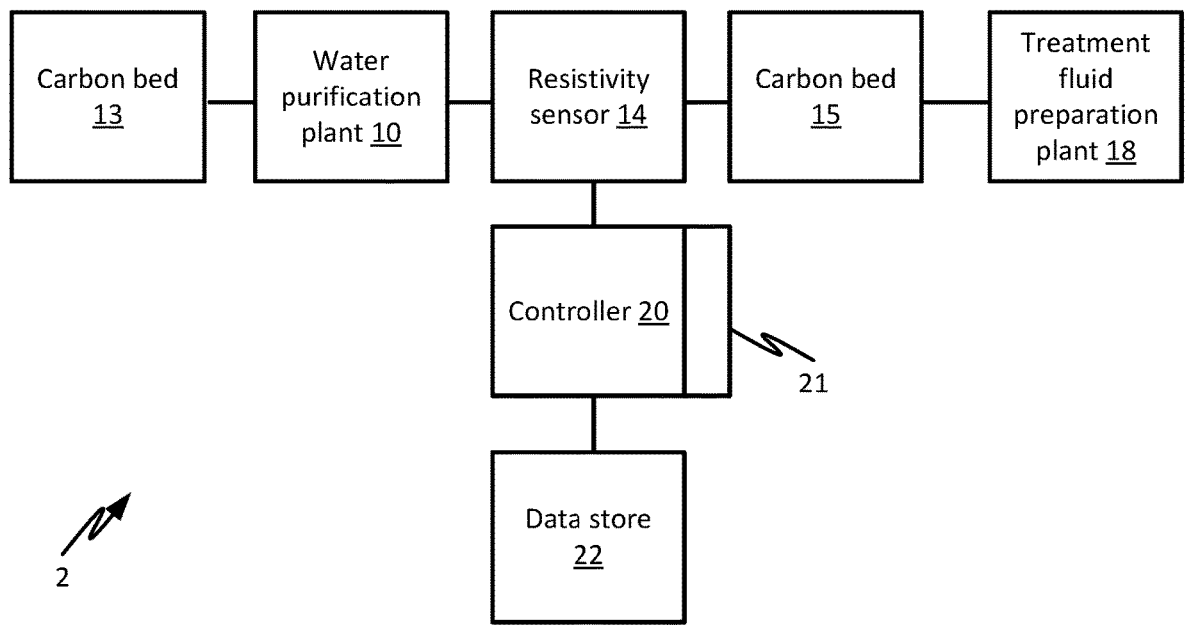
FIG. 5 shows a diagram of a water purification system in which chloramine levels are tested automatically and in which the chloramine removal stages include carbon filter beds, according to embodiments of the disclosed subject matter.

Referring to FIG. 5, in a water treatment system 2, similar to water treatment system 1 of FIG. 4, except that the chloramine removal stages 12 and 16 are provided specifically as carbon beds 13 and 15. In the embodiment of FIG. 5, the carbon bed 13 may be one or more replaceable carbon beds, and/or the carbon bed 15 may be one or more replaceable carbon beds. Thus, one or both of the carbon beds 13, 15 can be replaced when chloramine breakthrough is predicted by the controller 20 and output on the display 21. For example, upon detection of actual or predicted breakthrough by the controller 20, an indication may be provided to a user to replace the carbon bed at 13 with the carbon bed previously at 15 and to install a brand new carbon bed at 15.

To provide the ability to predict the exhaustion of the chloramine removal stage 12 (or carbon bed 13), the controller may be provided with apparatus to indicate cumulative flow of product water. By calculating the level of water production, extrapolating forward in time, and comparing the level of chloramine increase over a same time, the controller 20 may generate a prediction of when the chloramine removal stage 12 (or carbon bed 13) will reach exhaustion and output the prediction on the output device 21. The prediction capability described presently may be provided in all of the embodiments disclosed herein.

In other embodiments based on those of FIGS. 4 and 5, the chloramine removal stages 12 and 16 (or carbon beds 13 and 15) may be replaced with other types of filter stages such as reverse osmosis, electrodialysis, and other devices.

Figure 6:
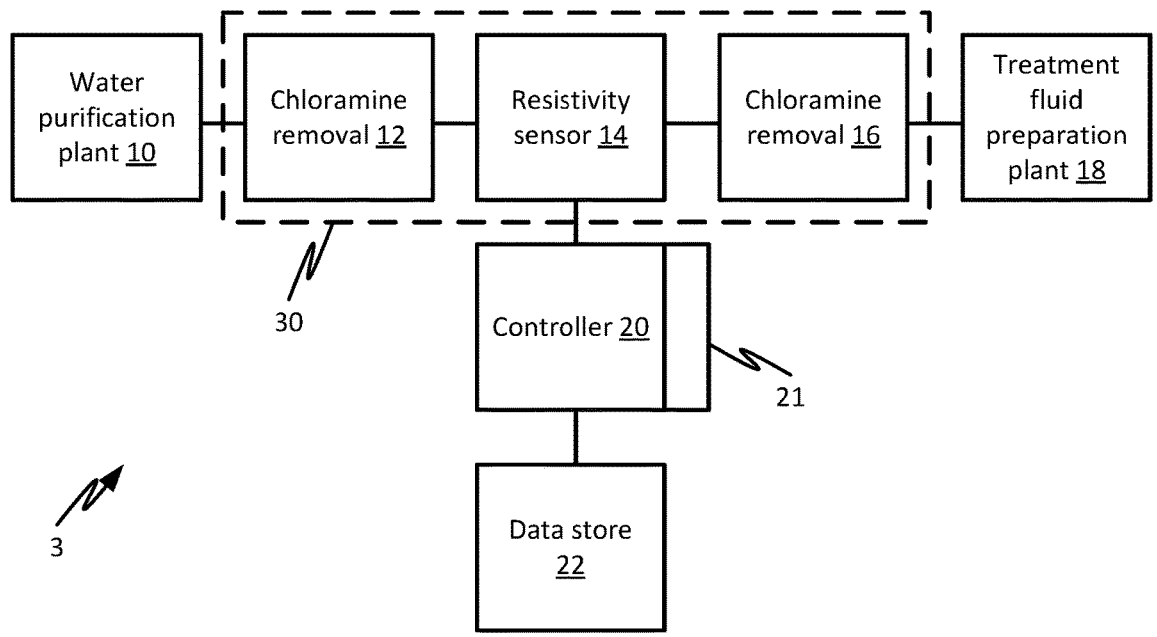
FIG. 6 shows a diagram of a water purification system in which chloramine levels are tested automatically and in which a replaceable component having one or more chloramine removal filtration stages has a resistivity cell combined with it, according to embodiments of the disclosed subject matter.

Referring to FIG. 6, a water treatment system 3 provides chloramine removal stages 12 and 16 and resistivity sensor 14 as a replaceable unit 30. In the water treatment system 3, the chloramine removal stage 16 may be of a different size from the chloramine removal stage 12. For example, the chloramine removal stage 16 may be smaller and thereby serve as a back-up stage to chloramine removal stage 12. In other respects, water treatment system 3 may have the features and properties of the foregoing embodiments.

Figure 7:
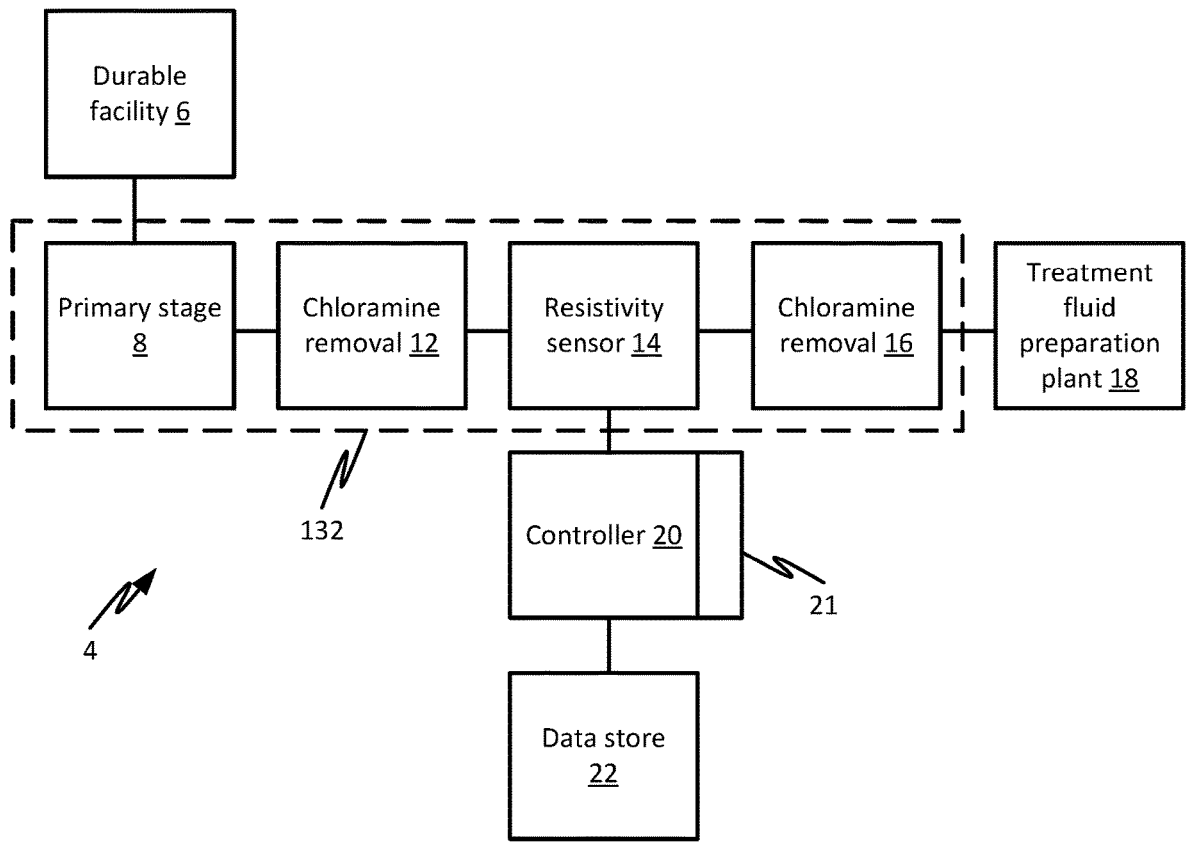
FIG. 7 shows a diagram of a water purification system in which chloramine levels are tested automatically and in which a replaceable component having a primary filtration stage and one or more chloramine removal filtration stages has a resistivity cell combined with it, according to embodiments of the disclosed subject matter.

Referring to FIG. 7, a water treatment system 4 provides chloramine removal stages 12 and 16 and resistivity sensor 14 as well as a primary stage 8 as a replaceable unit 132. Similar to the water treatment system 3 of FIG. 6, chloramine removal stage 16 may be of a different size from chloramine removal stage 12 in water treatment system 4. For example, the chloramine removal stage 16 may be smaller and thereby serve as a back-up stage to chloramine removal stage 12. Stages of filtration that have a longer life may be provided in a durable facility 6, which may include permanent fixtures and filter components that are replaced less frequently than those in replaceable unit 132. In other respects, water treatment system 3 may have the features and properties of the foregoing embodiments.

The primary stage 8 may be one or more filters for reducing contamination including particulate removal, ultraviolet treatment, or other types of filtration. The primary stage 8 may be omitted and is not essential to all of the disclosed embodiments. The durable facility 6 may include pumps, backflow preventers, and other elements. The durable facility may incorporate the primary stage 8 or it may be a separate unit. The durable facility 6 may also be present or omitted to form variants.

As in previous embodiments, stages of filtration that have a longer life may be provided in the durable facility 6, which may include permanent fixtures and filter components that are replaced less frequently than those in replaceable units 32 and 132 as indicated in FIGS. 5 and 7. In other respects, the water treatment system may have the features and properties of the foregoing embodiments.

Product water may be directly fed to a treatment fluid preparation plant 18 which may combine the product water with other materials to create a treatment fluid such as dialysate. In embodiments, a treatment fluid is provided to a blood treatment circuit under control of a blood treatment system which may be adapted to draw the treatment fluid on-demand. Alternatively, product water may be provided to any downstream consumer appliance or person.

Note that in all the above embodiments, the resistivity sensor 14 may be a contact-type device with a pair of conductors spaced apart by a fixed distance streamwise along a flow channel. The controller may include power and galvanic measurement elements to permit the controller to receive a signal from the resistivity sensor. The resistivity sensor 14 may operate on other principles as well. For example, it may capacitively drive a current through a predefined flow channel through non-wetted conductors according to known techniques.

In alternative embodiments, the downstream chloramine removal stage 16 (or carbon bed 15) is omitted.

Figure 8:
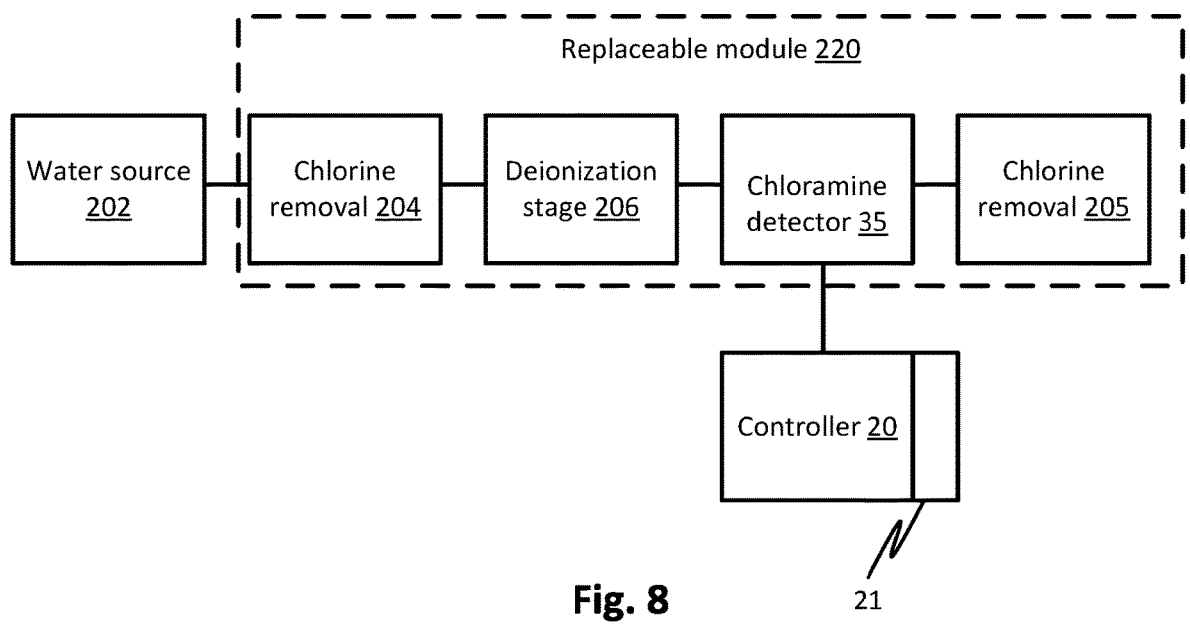
FIG. 8 shows a possible way of ordering and modularizing components of water filtration embodiments described herein, according to embodiments of the disclosed subject matter.

FIG. 8 shows a possible way of ordering and modularizing components of water filtration embodiments described herein according to embodiments of the disclosed subject matter. The drawing of FIG. 8 is generally consistent with many of the embodiments and claims hereinbelow. It shows a particular layout of a fluid path, controller, filter, and sensor elements and a modular configuration for replacement of certain components according to the filter replacement schedule determined by prediction of a time of replacement according to cumulative volume filtered since the filter was changed, cumulative time since the filter was changed, or a combination of the two. Other elements such as control valves and pumps may be provided to form various embodiments but are not shown or discussed with reference to the present figures. They may be used in any suitable combination and configuration to provide for the operation described with reference to any of the embodiments.

Examples of combining both cumulative time since filter change and cumulative volume since filter change include:

Reaching a predefined maximum time since filter change or a predefined maximum volume of water processed since filter change.

Reaching a predefined maximum time since filter change or a predefined maximum volume of water processed since filter change, where the predefined time is scaled according to the cumulative average rate of water processed so that an idle filter may be replaced more quickly than one that is used continuously.

A water source 202 may be, as any primary source of water disclosed herein, a tap, a batch of water, or water from a treatment plant. A replaceable module 220 is formed with a chlorine removal filter 204. The chlorine removal filter 204 identifies, in any of the embodiments herein, a chloramine removal filter, a carbon filter, or alternative examples such as a UV lamp. Thus the description of FIG. 8 shows alternative embodiments that may be generated using any of the embodiments having any of these types of chlorine removal filters. A deionization stage 206 is also part of the replaceable module 220, as is a chloramine detector 35 and, optionally, a further chlorine removal filter 205 which may be of any type identified with regard to chlorine removal filter 204. The controller 20 may be configured to predict the exhaustion of chlorine removal filter 204, and the deionization stage 206 may be sized such that its predicted exhaustion falls within the interval predicted for the chlorine removal filter 204. Optionally, the chlorine removal filter 205 can be provided in embodiments as a back-up. Although shown in this embodiment, a chlorine removal filter 205 serving as a backup may be provided in any of the embodiments. The chlorine removal filter 205 may be sized or have a filter capacity different from that of chlorine removal filter 204, for example, the backup filter can be smaller in size or capacity than the chlorine removal filter 204.

Figure 9:
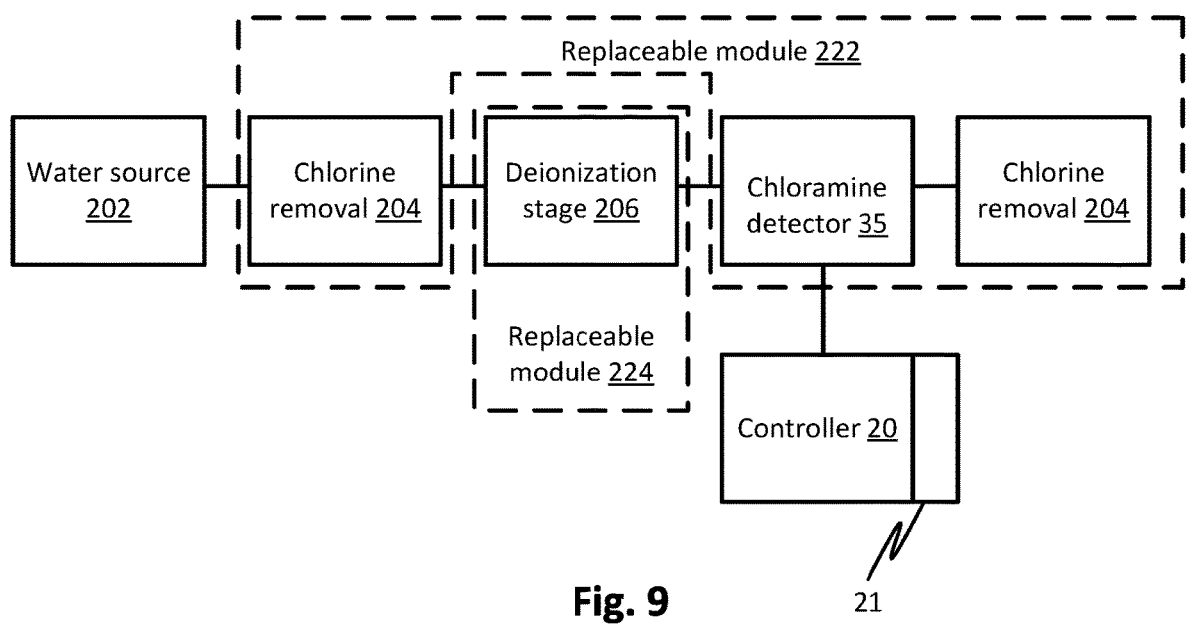
FIG. 9 shows a possible way of ordering and modularizing components of water filtration embodiments described herein, according to embodiments of the disclosed subject matter.

FIG. 9 shows another possible way of ordering and modularizing components of water filtration system embodiments described herein according to embodiments of the disclosed subject matter, for example to have a first replaceable module 222 with one or more chlorine removal filters 204 and a chloramine detector 35, and a second replaceable module 224 with a deionization filter stage 206.

Figure 10:
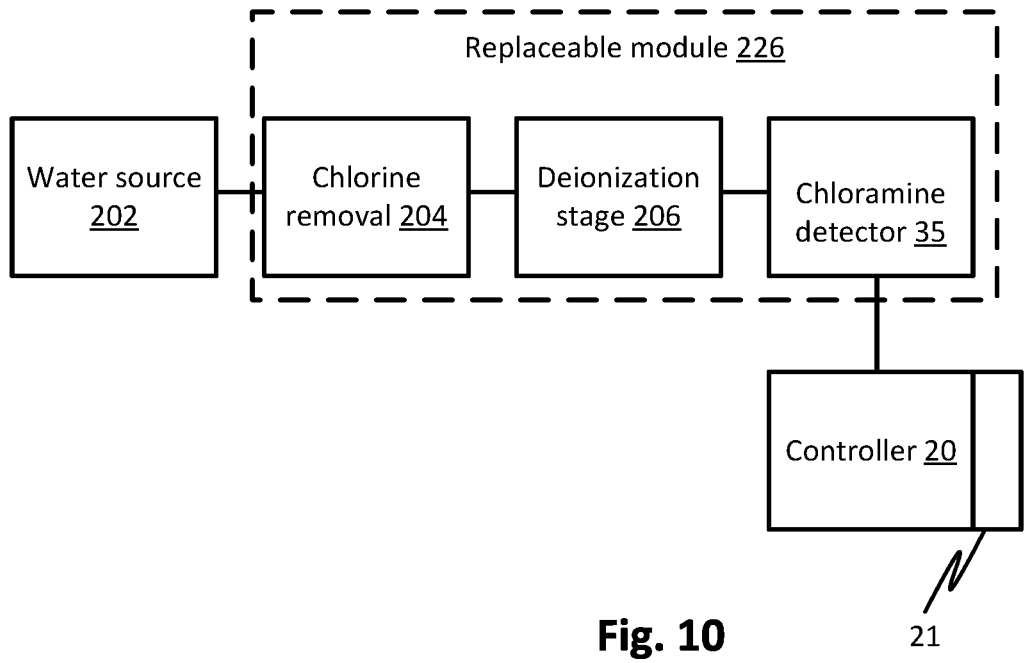
FIG. 10 shows a possible way of ordering and modularizing components of water filtration embodiments described herein, according to embodiments of the disclosed subject matter.

FIG. 10 shows another possible way of ordering and modularizing components of water filtration system embodiments described herein according to embodiments of the disclosed subject matter, for example, to have a replaceable module 226 with a chlorine removal filter 204, a deionization stage 206, and a chloramine detector 35.

Figure 11:
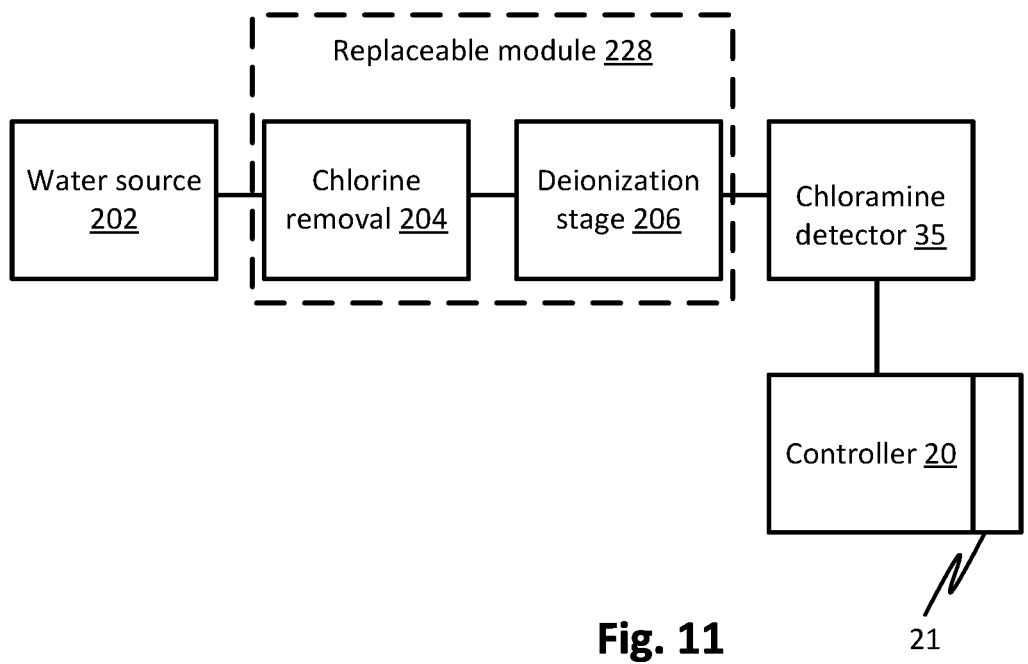
FIG. 11 shows a possible way of ordering and modularizing components of water filtration embodiments described herein, according to embodiments of the disclosed subject matter.

FIG. 11 shows another possible way of ordering and modularizing components of water filtration system embodiments described herein according to embodiments of the disclosed subject matter, for example, to have a replaceable module 228 with a chlorine removal filter 204 and a deionization stage 206.

Figure 12:
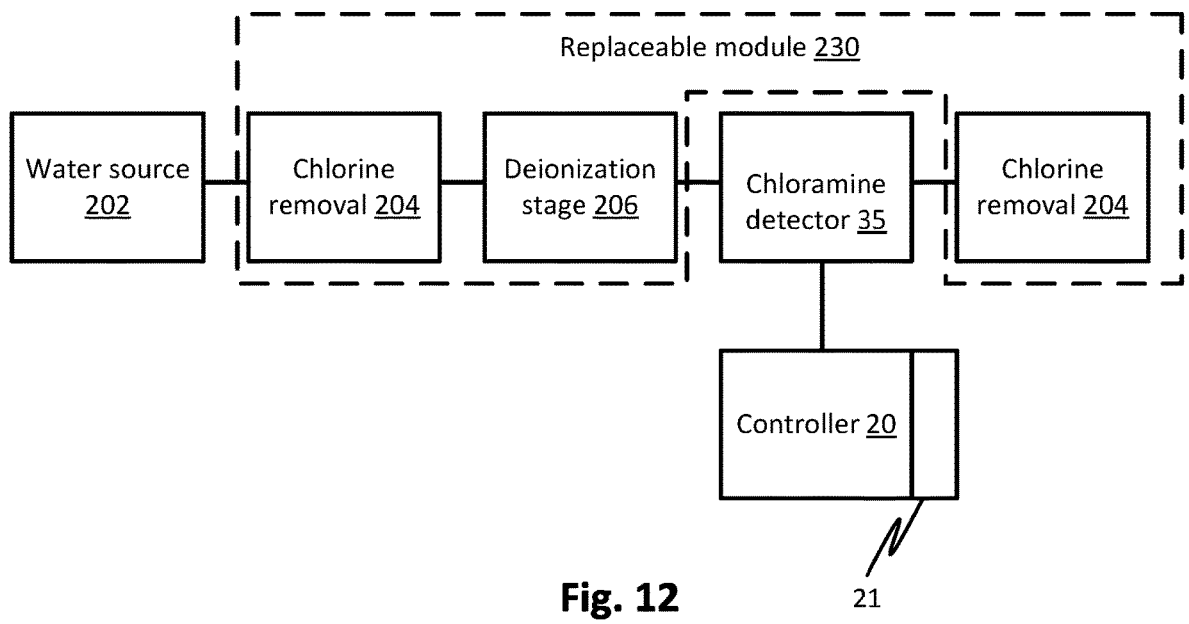
FIG. 12 shows a possible way of ordering and modularizing components of water filtration embodiments described herein, according to embodiments of the disclosed subject matter.

FIG. 12 shows another possible way of ordering and modularizing components of water filtration system embodiments described herein according to embodiments of the disclosed subject matter, for example, to have a replaceable module 230 with one or more chlorine removal filters 204 and a deionization stage 206.

Figure 13:
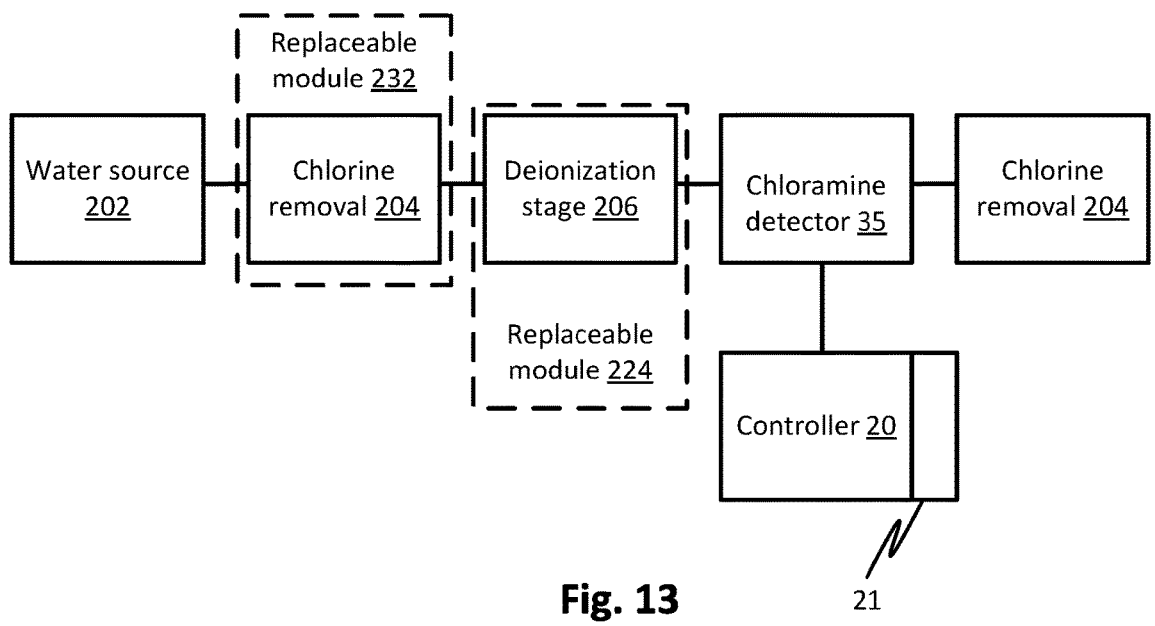
FIG. 13 shows a possible way of ordering and modularizing components of water filtration embodiments described herein, according to embodiments of the disclosed subject matter.

FIG. 13 shows another possible way of ordering and modularizing components of water filtration system embodiments described herein according to embodiments of the disclosed subject matter, for example to have a first replaceable module 232 with a chlorine removal filter 204 and a second replaceable module 224 with a deionization filter stage.

In any of the embodiments containing a chloramine detector or a resistivity sensor it should be clear from the discussion herein that the resistivity sensor may be replaced by a chloramine detector and that the latter may include both a resistivity sensor and a temperature sensor and provide a signal indicating concentration of ionic species including chlorine and chloramine.

Note that the controller 20 of any of the embodiments may include a data store 22 and may be configured as discussed with reference to FIGS. 4 and 5.

According to first embodiments thereof, a fluid processing system is adapted for providing purified water for a use in preparing dialysate and having no more than a predefined level of chloramine. In first embodiments, the fluid processing system can include a controller and a fluid circuit, the fluid circuit including at least one of a pump and a control valve, the controller being adapted for controlling said at least one of a pump and a control valve to permit the control of a product water from said fluid circuit. In first embodiments, the fluid circuit can include a replaceable activated carbon filter module configured to remove chloramine from primary water. In first embodiments, the fluid circuit connects a primary deionization filter to the activated carbon filter, the primary deionization filter being configured to remove ions from the water to produce first deionized water with a resistivity of more than 5 megohm-cm. In first embodiments, the fluid processing system comprises a first resistivity sensor positioned by the fluid circuit at the outlet of the primary deionization filter and adapted for indicating a resistivity of the first deionized water to detect exhaustion of said primary deionization filter, the controller being adapted to generate an exhaustion alarm signal responsively to said resistivity sensor. In first embodiments, the fluid processing system comprises a secondary deionization filter positioned by the fluid circuit at the outlet of the resistivity sensor from the first filter to provide a backup in the event of exhaustion of the primary deionization filter. In first embodiments, the fluid processing system comprises a chloramine detection element, including a second resistivity sensor and a temperature sensor, positioned by the fluid circuit at the outlet of the secondary deionization filter and configured to apply signals indicating temperature and resistivity to the controller. In first embodiments, the controller can store data for converting said signals indicating temperature and resistivity to data indicating a chloramine level and is configured to control the flow of product water responsively to said data indicating a chloramine level, the control of flow being effective to prevent the flow of product water in the event of a chloramine level higher than said predefined level. In first embodiments, the controller is further configured to generate a signal predicting when said activated carbon filter should be replaced, the predicting being responsive to at least one of a lapsed time since the first filter was replaced, a cumulative volume of water processed by said first filter, a quality of tap water processed thereby. In first embodiments, the fluid processing system comprises a proportioning system configured to mix the product water from the fluid circuit with dialysate concentrate to generate dialysate. In first embodiments, the fluid processing system comprises a medical treatment system connected to said proportioning system and configured to consume said dialysate in performing a dialysis treatment.

Any of the foregoing first embodiments may be varied to form additional first embodiments in which the replaceable activated carbon filter module is configured to be replaced as a modular unit. Any of the foregoing first embodiments may be varied to form additional first embodiments in which the replaceable activated carbon filter and the primary deionization filter module are configured to be replaced as a single modular unit. Any of the foregoing first embodiments may be varied to form additional first embodiments in which said first resistivity sensor is a flow through sensor and said controller is configured to continuously monitor the resistivity of a flow therethrough such that said generate an exhaustion alarm signal is generated immediately upon the detection of a resistivity associated with exhaustion of said primary deionization filter. Any of the foregoing first embodiments may be varied to form additional first embodiments in which said first resistivity sensor is a flow through sensor and said controller is configured to continuously monitor the resistivity of a flow therethrough such that said generate an exhaustion alarm signal is generated immediately upon the detection of a resistivity associated with exhaustion of said primary deionization filter. Any of the foregoing first embodiments may be varied to form additional first embodiments in which said first resistivity sensor is a flow through sensor and said controller is configured to continuously monitor the resistivity of a flow therethrough such that said generate an exhaustion alarm signal is generated immediately upon the detection of a resistivity associated with exhaustion of said primary deionization filter. Any of the foregoing first embodiments may be varied to form additional first embodiments in which the second resistivity sensor is a flow through sensor and said controller is configured to continuously monitor the resistivity of a flow therethrough such that a flow of product water is controlled immediately upon the detection of a resistivity associated with exhaustion of said primary deionization filter. Any of the foregoing first embodiments may be varied to form additional first embodiments in which said second resistivity sensor is a flow through sensor and said controller is configured to continuously monitor the resistivity of a flow therethrough such that a flow of product water is controlled immediately upon the detection of a resistivity associated with exhaustion of said primary deionization filter. Any of the foregoing first embodiments may be varied to form additional first embodiments in which said second resistivity sensor is a flow through sensor and said controller is configured to continuously monitor the resistivity of a flow therethrough such that a flow of product water is controlled immediately upon the detection of a resistivity associated with exhaustion of said primary deionization filter. Any of the foregoing first embodiments may be varied to form additional first embodiments in which said second resistivity sensor is a flow through sensor and said controller is configured to continuously monitor the resistivity of a flow therethrough such that a flow of product water is controlled immediately upon the detection of a resistivity associated with exhaustion of said primary deionization filter. Any of the foregoing first embodiments may be varied to form additional first embodiments in which said second resistivity sensor is a flow through sensor and said controller is configured to continuously monitor the resistivity of a flow therethrough such that a flow of product water is controlled immediately upon the detection of a resistivity associated with exhaustion of said primary deionization filter. Any of the foregoing first embodiments may be varied to form additional first embodiments in which said second resistivity sensor is a flow through sensor and said controller is configured to continuously monitor the resistivity of a flow therethrough such that a flow of product water is controlled immediately upon the detection of a resistivity associated with exhaustion of said primary deionization filter. Any of the foregoing first embodiments may be varied to form additional first embodiments in which said controller has a user interface and said controller is further configured to selectively output an indication of excessive chloramine levels responsively to said data indicating a chloramine level. Any of the foregoing first embodiments may be varied to form additional first embodiments in which said controller has a user interface and said controller is further configured to selectively output an indication of excessive chloramine levels responsively to said data indicating a chloramine level. Any of the foregoing first embodiments may be varied to form additional first embodiments in which said controller has a user interface and said controller is further configured to selectively output an indication of excessive chloramine levels responsively to said data indicating a chloramine level.

According to second embodiments thereof, a fluid processing system comprises a fluid circuit including a replaceable first filter module configured to remove chloramine from primary water and a resistivity testing element positioned downstream of the first filter module such that filtered water from the first filter module is tested thereby to detect for a threshold level of chloramine remaining in the filtered water. In second embodiments, the resistivity testing element being adapted to detect resistivity above 2.5 megohm-cm. In second embodiments, the fluid processing system comprises a medical treatment device adapted for receiving product water according to demand by the medical treatment device, the medical treatment device including medicament preparation component. In second embodiments, the first filter module, or a deionization filter upstream or downstream of the first filter module, is adapted to increase a resistivity of the filtered water received by the resistivity testing element, to a level higher than a predefined water quality requirement forming part of a medical treatment standard to which the medical treatment device is subject. In second embodiments, the fluid processing system comprises a controller configured to control a flow of water in the fluid circuit and to output an alarm signal. In second embodiments, the resistivity testing element is adapted to apply to the controller a resistivity signal indicating a resistivity of the filtered water received thereby and the controller being configured to control the flow of filtered water responsively to the resistivity signal such that said controller, in response to a resistivity above a predefined level of more than 2.5 megohm-cm, or a rate of change of a resistivity above a predefined rate, causes said controller to output a signal indicating a water quality error. In second embodiments, the controller is further configured to determine a time for replacement of said first filter module and to output an alarm signal indicating that said first filter module should be replaced, the time for replacement being determined based on a measured total volume and/or a total time since a last replacement of the first filter module and taking into account a predicted primary water quality, to ensure that only a fraction less than 100% of a chloramine removal capacity of the first filter module has been consumed by said time for replacement.

Any of the foregoing second embodiments may be varied to form additional second embodiments in which the predefined level is more than 4 megohm-cm. Any of the foregoing second embodiments may be varied to form additional second embodiments in which the predefined level is more than 6 megohm-cm. Any of the foregoing second embodiments may be varied to form additional second embodiments in which the predefined level is more than 8 megohm-cm. Any of the foregoing second embodiments may be varied to form additional second embodiments in which the predefined level is at least 10 megohm-cm. Any of the foregoing second embodiments may be varied to form additional second embodiments in which the first filter module includes an activated carbon filter. Any of the foregoing second embodiments may be varied to form additional second embodiments in which the fluid processing system comprises a deionization filter upstream or downstream of the first filter module, wherein the first filter module includes an activated carbon filter. Any of the foregoing second embodiments may be varied to form additional second embodiments in which the first filter module includes an activated carbon filter and a deionization filter which are configured to be replaced as a modular unit. Any of the foregoing second embodiments may be varied to form additional second embodiments in which the medical treatment device includes medicament preparation component that is adapted receive product water from the resistivity testing element and generated a medicament therefrom. Any of the foregoing second embodiments may be varied to form additional second embodiments in which the fluid processing system comprises a medicament-consuming component that received medicament from the medicament preparation component and is adapted to deliver a medical treatment to a patient. Any of the foregoing second embodiments may be varied to form additional second embodiments in which the medicament preparation component includes a dialysate preparation component. Any of the foregoing second embodiments may be varied to form additional second embodiments in which the dialysate preparation component includes a proportioning device adapted to mix medicament concentrate with product water by generating a mechanical or electronic command signal to convey product water. Any of the foregoing second embodiments may be varied to form additional second embodiments in which the resistivity testing element includes a temperature sensor and the resistivity testing element, the controller being adapted for controlling said fluid circuit responsively to a resistance signal generated by said resistivity testing element and a temperature signal generated by said temperature sensor. Any of the foregoing second embodiments may be varied to form additional second embodiments in which the resistivity testing element has a flow-through configuration adapted to detect resistivity continuously as fluid flows therethrough. Any of the foregoing second embodiments may be varied to form additional second embodiments in which the fluid circuit includes at least one pump controlled by said controller responsively to said resistivity above a predefined level. Any of the foregoing second embodiments may be varied to form additional second embodiments in which the fluid circuit includes at least one pump controlled by said controller to halt said at least one pump responsively to said resistivity above a predefined level. Any of the foregoing second embodiments may be varied to form additional second embodiments in which the fluid circuit includes at least one pump controlled by said controller responsively to said resistivity above a predefined level or wherein the fluid circuit includes at least one pump controlled by said controller to halt said at least one pump responsively to said resistivity above a predefined level. Any of the foregoing second embodiments may be varied to form additional second embodiments in which the fluid circuit includes at least one control valve controlled by said controller responsively to said resistivity above a predefined level. Any of the foregoing second embodiments may be varied to form additional second embodiments in which the fluid circuit includes at least one control valve controlled by said controller to halt or divert a flow of water using at least one control valve responsively to said resistivity above a predefined level. Any of the foregoing second embodiments may be varied to form additional second embodiments in which the fluid circuit includes at least one control valve controlled by said controller responsively to said resistivity above a predefined level. Any of the foregoing second embodiments may be varied to form additional second embodiments in which the fluid circuit includes at least one pump controlled by said controller to halt or divert a flow of water using said at least one control valve responsively to said resistivity above a predefined level. Any of the foregoing second embodiments may be varied to form additional second embodiments in which the fluid processing system further comprises a second filter module configured to remove chloramine.

According to third embodiments thereof, a method of delivering a blood treatment comprises carbon-filtering primary tap water to generate substantially chloramine-free water, deionizing the substantially chloramine-free water to a predetermined level of resistivity, to generate deionized product water, the predetermined level being selected to be low enough to permit a detection of chloramine in the deionized product water resulting from a failure of said carbon-filtering, and determining, responsively to time and/or cumulative volume of substantially chloramine-free water generated by said carbon-filtering, that at least one carbon filter used to perform said carbon-filtering is to be replaced and, responsively to said determining, outputting a command signal to replace said at least one carbon filter. In third embodiments, said determining is effective to ensure that a chloramine level in said deionized product water is below a predetermine safe level for use in a dialysis, hemodiafiltration, or hemofiltration treatment of a human, said predefined safe level being according to a predefined medical standard with a margin for safety based on a predicted water quality and a predicted chloramine removing efficacy of said at least one carbon filter. In third embodiments, the method comprises ensuring in the event an error in said carbon-filtering, that said deionized product water is safe, detecting chloramine in the deionized product water resulting from a failure of said carbon-filtering and controlling a flow of said deionized product water responsively thereto.

Any of the foregoing third embodiments may be varied to form additional third embodiments in which the controlling a flow includes halting a flow of said deionized product water. Any of the foregoing third embodiments may be varied to form additional third embodiments in which the controlling a flow includes generating a command to halt a flow of said deionized product water. Any of the foregoing third embodiments may be varied to form additional third embodiments in which the controlling a flow includes generating a user interface output indicating an error in the level of chloramine in said deionized product water. Any of the foregoing third embodiments may be varied to form additional third embodiments in which the method further comprises supplying said deionized product water to a proportioning system to generate a medicament therefrom and making said medicament available for a blood treatment. Any of the foregoing third embodiments may be varied to form additional third embodiments in which the predetermined level of resistivity is determined responsively to a temperature of the deionized product water. Any of the foregoing third embodiments may be varied to form additional third embodiments in which the level of resistivity is at least 2.5 megohm-cm. Any of the foregoing third embodiments may be varied to form additional third embodiments in which the predefined level of resistivity is more than 4 megohm-cm. Any of the foregoing third embodiments may be varied to form additional third embodiments in which the predefined level of resistivity is more than 6 megohm-cm. Any of the foregoing third embodiments may be varied to form additional third embodiments in which the predefined level of resistivity is more than 8 megohm-cm. Any of the foregoing third embodiments may be varied to form additional third embodiments in which the predefined level of resistivity is at least 10 megohm-cm. Any of the foregoing third embodiments may be varied to form additional third embodiments in which the level of resistivity is at least 2.5 megohm-cm. Any of the foregoing third embodiments may be varied to form additional third embodiments in which the predefined level of resistivity is more than 4 megohm-cm. Any of the foregoing third embodiments may be varied to form additional third embodiments in which the predefined level of resistivity is more than 6 megohm-cm. Any of the foregoing third embodiments may be varied to form additional third embodiments in which the predefined level of resistivity is more than 8 megohm-cm. Any of the foregoing third embodiments may be varied to form additional third embodiments in which the predefined level of resistivity is at least 10 megohm-cm. Any of the foregoing third embodiments may be varied to form additional third embodiments in which the predefined level of resistivity is selected based on a minimum level required to reliably detect a presence of chloramine in said deionized product water.

According to fourth embodiments thereof, a method for purifying water produces a product water meeting a predefined water quality requirement that includes a predefined limit on the amount of a specific dissolved species that is weakly conductive and a lower limit on the allowed resistivity of said product water due to all dissolved species. In fourth embodiments, the method comprises removing the specific dissolved species from a primary water stream using a first filter to produce primary water depleted of the specific dissolved species and using a second filter, filtering the primary water depleted of the specific dissolved species to reduce other dissolved species sufficient to produce high resistivity product water whose resistivity is sufficiently high to permit the detection of the specific dissolved species using a resistivity detector. In fourth embodiments, the method further comprises using a controller, predicting, based on a parameter that is responsive to time of use of the first filter, and outputting from the controller, a first signal indicating a requirement to replace the first filter, the predicting being such that there is a sufficient remaining capacity to remove the specific dissolved species from the primary water stream to ensure that said product water meets said predefined limit on the amount of a specific dissolved species under non-error conditions. In fourth embodiments, the method further comprises using the controller, monitoring the resistivity of the high resistivity product water and generating a second signal indicating the detection of a product water quality error responsively to said monitoring, whereby, in the event of a failure of the predicting adequately to ensure that said product water meets said predefined limit on the amount of a specific dissolved species.

Any of the foregoing fourth embodiments may be varied to form additional fourth embodiments in which the non-error conditions include a range of primary water quality. Any of the foregoing fourth embodiments may be varied to form additional fourth embodiments in which the first filter includes a filter that removes the specific dissolved species using an adsorbent and the second filter uses a chemical reaction to remove ions from the primary water depleted of the specific dissolved species. Any of the foregoing fourth embodiments may be varied to form additional fourth embodiments in which the first filter includes activated carbon. Any of the foregoing fourth embodiments may be varied to form additional fourth embodiments in which the controller is a programmable controller with a flow sensor that performs said predicting responsively to a signal from the said flow sensor and such that said predicting is responsive to a cumulative historical flow since the first filter was replaced. Any of the foregoing fourth embodiments may be varied to form additional fourth embodiments in which the controller is a programmable controller, with a timer, that performs said predicting responsively to said timer and such that said predicting is responsive to a cumulative time since the first filter was replaced. Any of the foregoing fourth embodiments may be varied to form additional fourth embodiments in which the controller is a programmable controller, with a timer, that performs said predicting responsively to said timer and such that said predicting is responsive to a cumulative time since the first filter was replaced. Any of the foregoing fourth embodiments may be varied to form additional fourth embodiments in which said second filter includes a deionization filter. Any of the foregoing fourth embodiments may be varied to form additional fourth embodiments in which the product water is generated at a treatment site and said method further includes generating a medicament for use in performing a blood treatment. Any of the foregoing fourth embodiments may be varied to form additional fourth embodiments in which the specific dissolved species includes chlorine or compounds thereof. Any of the foregoing fourth embodiments may be varied to form additional fourth embodiments in which the product water is generated at a treatment site and said method further includes generating a medicament and made available for use in performing a blood treatment. Any of the foregoing fourth embodiments may be varied to form additional fourth embodiments in which the method does not include routine chemical testing for said specific dissolved species.

According to fifth embodiments thereof, a system for purifying water produces a product water meeting a predefined water quality requirement that includes a predefined limit on the amount of a specific dissolved species that is weakly conductive and a lower limit on the allowed resistivity of said product water due to all dissolved species. In fifth embodiments, the system comprises a first filter adapted for removing the specific dissolved species from a primary water stream to produce primary water depleted of the specific dissolved species and a second filter connected to receive the primary water depleted of the specific dissolved species, the second filter being adapted to reduce other dissolved species sufficient to produce high resistivity product water whose resistivity is sufficiently high to permit the detection of the specific dissolved species using a resistivity detector. In fifth embodiments, the system further comprises a controller configured to predict, based on at least one parameter that is responsive to time of use of the first filter, and to output a first signal indicating a requirement to replace the first filter, the controller being configured to predict such that there is, at all times, a sufficient remaining capacity to remove the specific dissolved species from the primary water stream to ensure that said product water meets said predefined limit on the amount of a specific dissolved species under non-error conditions. In fifth embodiments, the system further comprises a resistivity sensor connected to the controller and connected to the first filter such that the product water from the second filter flows therethrough. In fifth embodiments, the controller is further configured to monitor the resistivity of the high resistivity product water indicated by the resistivity sensor and to generate a second signal indicating the detection of a product water quality error responsively to the resistivity sensor, whereby, in the event of a failure of the predicting adequately to ensure that said product water meets said predefined limit on the amount of a specific dissolved species.

Any of the foregoing fifth embodiments may be varied to form additional fifth embodiments in which the non-error conditions include a range of primary water quality. Any of the foregoing fifth embodiments may be varied to form additional fifth embodiments in which the first filter includes a filter that removes the specific dissolved species using an adsorbent and the second filter uses a chemical reaction to remove ions from the primary water depleted of the specific dissolved species. Any of the foregoing fifth embodiments may be varied to form additional fifth embodiments in which the first filter includes activated carbon. Any of the foregoing fifth embodiments may be varied to form additional fifth embodiments in which the controller is a programmable controller, with a flow sensor, said at least one parameter including a signal from the said flow sensor such that said predicting is responsive to a cumulative historical flow since the first filter was replaced. Any of the foregoing fifth embodiments may be varied to form additional fifth embodiments in which the controller is a programmable controller, with a timer, said at least one parameter including a time indication from said timer and such that said predicting is responsive to a cumulative time since the first filter was replaced. Any of the foregoing fifth embodiments may be varied to form additional fifth embodiments in which the controller is a programmable controller, with a timer, said at least one parameter including an indication from said timer and such that said predicting is responsive to a cumulative time since the first filter was replaced. Any of the foregoing fifth embodiments may be varied to form additional fifth embodiments in which said second filter includes a deionization filter. Any of the foregoing fifth embodiments may be varied to form additional fifth embodiments in which the second filter is connected to a proportioning system used for generating a medicament for use in performing a blood treatment. Any of the foregoing fifth embodiments may be varied to form additional fifth embodiments in which the system further comprises a proportioning system connected to receive the product water from the second filter, the proportioning system being configured to generate a medicament from the product water for use in performing a blood treatment. Any of the foregoing fifth embodiments may be varied to form additional fifth embodiments in which the specific dissolved species includes chlorine or compounds thereof. Any of the foregoing fifth embodiments may be varied to form additional fifth embodiments in which the product water is generated at a treatment site and said system further includes generating a medicament and made available for use in performing a blood treatment. Any of the foregoing fifth embodiments may be varied to form additional fifth embodiments in which the system further comprises a proportioning system connected to receive the product water from the second filter, the proportioning system being configured to generate a medicament from the product water, and a medical treatment system configured to perform a blood treatment connected to receive the medicament from the proportioning system and to use said medicament in performing said blood treatment.

According to sixth embodiments thereof, a method for purifying water for making a medicament for a medical treatment can comprise purifying water and supplying a product water resulting from said purifying to a proportioning system configured to generate a medicament for a medical treatment and using a controller, continuously monitoring for a threshold concentration of chloramine in said product water and generating an alarm signal responsively to said monitoring. In sixth embodiments, said monitoring includes continuously detecting a resistivity of said product water and a temperature of said product water. In sixth embodiments, the method further comprises controlling a flow of product water to said proportioning system responsively to said alarm signal.

Any of the foregoing sixth embodiments may be varied to form additional sixth embodiments in which the threshold concentration corresponds to a resistivity level of at least 2.5 megohm-cm. Any of the foregoing sixth embodiments may be varied to form additional sixth embodiments in which the purifying water includes passing water through an activated carbon filter. Any of the foregoing sixth embodiments may be varied to form additional sixth embodiments in which the purifying water includes passing water from the activated carbon filter through a deionization filter. Any of the foregoing sixth embodiments may be varied to form additional sixth embodiments in which the method further comprises mixing medicament concentrate with the purified product water using the proportioning system so as to generate said medicament. Any of the foregoing sixth embodiments may be varied to form additional sixth embodiments in which the monitoring includes passing the product water through a flow-through resistivity testing element adapted to continuously detect the resistivity of the product water. Any of the foregoing sixth embodiments may be varied to form additional sixth embodiments in which the controlling a flow of product water comprises halting the flow of product water responsively to said alarm signal.

According to seventh embodiments thereof, a method for purifying water for making a medicament for a medical treatment comprises purifying water and supplying a product water resulting from said purifying to a proportioning system configured to generate a medicament for a medical treatment, and using a controller, continuously monitoring for a threshold concentration of chloramine in said product water and generating an alarm signal responsively to said monitoring. In seventh embodiments, the monitoring includes continuously detecting a resistivity of said product water and a temperature of said product water.

Any of the foregoing seventh embodiments may be varied to form additional seventh embodiments in which the threshold concentration corresponds to a resistivity level of at least 2.5 megohm-cm. Any of the foregoing seventh embodiments may be varied to form additional seventh embodiments in which the purifying water includes passing water through an activated carbon filter. Any of the foregoing seventh embodiments may be varied to form additional seventh embodiments in which the purifying water includes passing water from the activated carbon filter through a deionization filter. Any of the foregoing seventh embodiments may be varied to form additional seventh embodiments in which the method further comprises mixing medicament concentrate with the purified product water using the proportioning system so as to generate said medicament. Any of the foregoing seventh embodiments may be varied to form additional seventh embodiments in which the monitoring includes passing the product water through a flow-through resistivity testing element adapted to continuously detect the resistivity of the product water.

According to eighth embodiments thereof, a method for purifying water for making a medicament for a medical treatment, comprises carbon filtering and deionizing water and supplying a product water resulting therefrom for use in making a medicament for a medical treatment. In eighth embodiments, the deionizing includes passing through a primary deionization filter stage and a backup deionization filter. In eighth embodiments, the method further comprises using a first ionic species detector that includes a first resistivity sensor, monitoring for a threshold level of dissolved species in the water emanating from the primary deionization filter including measuring resistivity of said water emanating from the primary deionization filter and generating a first alarm signal responsively to said monitoring for a threshold level of dissolved species in the water emanating from the primary deionization filter. In eighth embodiments, the method further comprises using a second ionic species detector that includes a second resistivity sensor, monitoring for a threshold level of chloramine in product water from the backup deionization filter and generating a second alarm signal responsively to said monitoring for a threshold level of chloramine in product water from the backup deionization filter.

Any of the foregoing eighth embodiments may be varied to form additional eighth embodiments in which the method further comprises generating a first respective alarm signal responsively to said monitoring for a threshold level of dissolved species. Any of the foregoing eighth embodiments may be varied to form additional eighth embodiments in which further comprises generating a second respective alarm signal responsively to said monitoring for a threshold level of chloramine. Any of the foregoing eighth embodiments may be varied to form additional eighth embodiments in which both of said monitoring includes continuously detecting a resistivity of water such that an alarm is generated immediately upon either of said thresholds being met. Any of the foregoing eighth embodiments may be varied to form additional eighth embodiments in which the threshold rate of chloramine corresponds to a resistivity level of at least 2.5 megohm-cm. Any of the foregoing eighth embodiments may be varied to form additional eighth embodiments in which the carbon filtering is performed before the deionizing. Any of the foregoing eighth embodiments may be varied to form additional eighth embodiments in which the method further comprises mixing medicament concentrate with the purified product water using a proportioning system so as to generate said medicament. Any of the foregoing eighth embodiments may be varied to form additional eighth embodiments in which the second resistivity sensor is a flow-through resistivity testing element adapted to continuously detect the resistivity of the product water. Any of the foregoing eighth embodiments may be varied to form additional eighth embodiments in which the method further comprises controlling a flow of product water responsively to at least one of said first and second alarm signals.

According to ninth embodiments thereof, a water purification system for generating medicament comprises at least one filter module constructed to receive a supply of water and to generate purified product water therefrom and a first sensor disposed downstream of the filter module and constructed to continuously detect a resistivity of the product water from the filter module, the sensor generating a first signal responsively to the detected resistivity. In ninth embodiments, the water purification system further comprises a second sensor constructed to measure temperature of the product water and to generate a second signal responsively to the measured temperature, and a controller coupled to the first and second sensors to receive said first and second signals, the controller being configured to monitor for a threshold concentration of chloramine in said product water responsively to the detected resistivity and the measured temperature.

Any of the foregoing ninth embodiments may be varied to form additional ninth embodiments in which the system further comprises at least one of a pump or valve that controls flow of the product water, the controller being operatively coupled to said at least one of a pump or valve, the controller being configured to control said at least one of a pump or valve responsively to the monitored concentration of chloramine. Any of the foregoing ninth embodiments may be varied to form additional ninth embodiments in which the controller is further configured to generate an alarm signal responsively to the monitored concentration of chloramine. Any of the foregoing ninth embodiments may be varied to form additional ninth embodiments in which the at least one filter module comprises an activated carbon filter. Any of the foregoing ninth embodiments may be varied to form additional ninth embodiments in which the at least one filter module comprises a deionization filter downstream from an activated carbon filter. Any of the foregoing ninth embodiments may be varied to form additional ninth embodiments in which the first sensor is a flow-through resistivity testing element adapted to continuously detect the resistivity of product water passing therethrough. Any of the foregoing ninth embodiments may be varied to form additional ninth embodiments in which the system further comprises a third sensor constructed to detect a resistivity of water passing from a first of the filter modules to a second of the filter modules, the first sensor being disposed downstream of both the first and second filter modules.

According to tenth embodiments thereof, a system for generating medicament comprises at least one filter module constructed to receive a supply of water and to generate purified product water therefrom, and a first sensor disposed downstream of the filter module and constructed to continuously detect a resistivity of the product water from the filter module, the sensor generating a first signal responsively to the detected resistivity. In tenth embodiments, the system further comprises a second sensor constructed to measure temperature of the product water and to generate a second signal responsively to the measured temperature, and a controller coupled to the first and second sensors to receive said first and second signals, the controller being configured to monitor for a threshold concentration of chloramine in said product water responsively to the detected resistivity and the measured temperature. In tenth embodiments, the system further comprises a proportioning system configured to mix the purified product water with a medicament concentrate to generate said medicament.

Any of the foregoing tenth embodiments may be varied to form additional tenth embodiments in which the system further comprises at least one of a pump or valve that controls flow of the product water, the controller being operatively coupled to said at least one of a pump or valve, the controller being configured to control said at least one of a pump or valve responsively to the monitored concentration of chloramine to halt product water flow to the proportioning system. Any of the foregoing tenth embodiments may be varied to form additional tenth embodiments in which the controller is further configured to generate an alarm signal responsively to the monitored concentration of chloramine. Any of the foregoing tenth embodiments may be varied to form additional tenth embodiments in which the at least one filter module comprises an activated carbon filter. Any of the foregoing tenth embodiments may be varied to form additional tenth embodiments in which the at least one filter module comprises a deionization filter downstream from an activated carbon filter. Any of the foregoing tenth embodiments may be varied to form additional tenth embodiments in which the first sensor is a flow-through resistivity testing element adapted to continuously detect the resistivity of product water passing therethrough. Any of the foregoing tenth embodiments may be varied to form additional tenth embodiments in which the system further comprises a third sensor constructed to detect a resistivity of water passing from a first of the filter modules to a second of the filter modules, the first sensor being disposed downstream of both the first and second filter modules.

According to eleventh embodiments thereof, a method for purifying water comprises filtering tap water to remove a first ionic species using a first filter to generate first filtered water, and calculating, using a controller, whether the first filter should be replaced based on data stored in said controller indicating a lapsed time since the first filter was replaced, a cumulative volume of water processed by said first filter, a quality of tap water processed thereby, or a combination of these. In eleventh embodiments, the method further comprises by said controller, outputting, responsively to said calculating, a first alarm signal indicating that said first filter is to be replaced, and using a first deionization filter stage, deionizing said first filtered water to produce first deionized water. In eleventh embodiments, the method further comprises detecting a level of second ionic species in said first deionized water and determining whether said first deionization filter stage is exhausted responsively to said detecting a level of second ionic species. In eleventh embodiments, the method further comprises by said controller, outputting, responsively to said determining, a second alarm signal indicating that said first deionization filter stage is to be replaced. In eleventh embodiments, the method further comprises using a second deionization filter stage, further deionizing said first deionized water to produce deionized product water, and detecting a level of said first ionic species in said deionized product water and outputting a third alarm signal responsively detecting a level of said first ionic species.

Any of the foregoing eleventh embodiments may be varied to form additional eleventh embodiments in which said first ionic species is chloramine. Any of the foregoing eleventh embodiments may be varied to form additional eleventh embodiments in which said first, second, and third alarm signals are electronic signals internal to the controller, the controller being configured to control a flow of product water responsively to at least one of said first, second, and third alarm signals. Any of the foregoing eleventh embodiments may be varied to form additional eleventh embodiments in which said detecting a level of first ionic species includes converting, using calibration data, temperature and resistivity measurements of said second deionized water, wherein said calibration data represents levels of chloramine corresponding to various combinations of temperature and resistivity of water. Any of the foregoing eleventh embodiments may be varied to form additional eleventh embodiments in which the calibration data is stored in the controller as a look up table or a formula. Any of the foregoing eleventh embodiments may be varied to form additional eleventh embodiments in which the first filter includes an activated carbon bed. Any of the foregoing eleventh embodiments may be varied to form additional eleventh embodiments in which the first filter is configured to reduce a chloramine level in said first filtered water to a predefined level, said controller being configured to generate said third alarm signal when said detecting a level of said first ionic species indicates a level exceeding said predefined level.

According to twelfth embodiments thereof, a water purification system for medicament preparation comprises a chloramine removal filter stage and a deionization filter stage adapted for receiving raw water and filtering the same to produce product water suitable for use in a medicament. In twelfth embodiments, the system further comprises a controller and a flow control element adapted to control a flow of water through said chloramine filter stage and said deionization filter stage. In twelfth embodiments, the system further comprises a chloramine sensor configured to continuously monitor a level of chloramine in said product water and apply at least a signal indicating resistivity of said product water to said controller. In twelfth embodiments, the controller is configured to control a flow of water responsively to said at least a signal.

Any of the foregoing twelfth embodiments may be varied to form additional twelfth embodiments in which the controller includes a data store that stores data that permits a level of chloramine to be determined from a combination of resistivity and temperature measurements of water that flows in said chloramine sensor. Any of the foregoing twelfth embodiments may be varied to form additional twelfth embodiments in which said chloramine sensor includes a resistivity cell adapted for measuring fluid resistance and temperature of a fluid flowing therethrough. Any of the foregoing twelfth embodiments may be varied to form additional twelfth embodiments in which said chloramine sensor includes a resistivity cell adapted for measuring fluid resistance and temperature of a fluid flowing therethrough and said controller includes a data store that stores data that permits a level of chloramine to be determined from a combination of resistivity and temperature measurements of water that flows in said chloramine sensor. Any of the foregoing twelfth embodiments may be varied to form additional twelfth embodiments in which said chloramine sensor includes a resistivity cell adapted for measuring fluid resistance and temperature of a fluid flowing therethrough and said controller includes a data store that stores data with calibration data representing a level of chloramine corresponding to combinations of resistivity and temperature. Any of the foregoing twelfth embodiments may be varied to form additional twelfth embodiments in which said chloramine sensor includes a resistivity cell adapted for measuring fluid resistance and temperature of a fluid flowing therethrough and said controller includes a data store that stores data with calibration data experimentally derived from tests of chloramine-containing water and adapted to represent a level of chloramine corresponding to combinations of resistivity and temperature.

According to thirteenth embodiments thereof, a fluid processing system is adapted for providing purified water for a use requiring water with a resistivity of no more than a use level. In thirteenth embodiments, the fluid processing system comprises a fluid circuit including a replaceable first filter module configured to remove chloramine from primary water and a resistivity testing element positioned downstream of the first filter module such that filtered water from the first filter module is tested thereby to detect a level of chloramine remaining in the filtered water. In thirteenth embodiments, the resistivity testing element is adapted to indicate resistivities exceeding said use level. In thirteenth embodiments, the first filter module, or a deionization filter upstream or downstream of the first filter module, is adapted to filter water so as to achieve a resistivity of the water filtered thereby, and received by the resistivity testing element, to a level higher than the use level. In thirteenth embodiments, the fluid processing system further comprises a controller connected to the resistivity testing element, configured to control a flow of water in the fluid circuit, and to output an alarm signal. In thirteenth embodiments, the resistivity testing element is connected to apply, to the controller, a resistivity signal indicating a resistivity of the filtered water received thereby and the controller being configured to control the flow of filtered water responsively to the resistivity signal such that said controller, in response to a resistivity above a predefined level above said use level, or a rate of change of a resistivity above a predefined rate, causes said controller to output a signal indicating a level of chloramine above a predetermined allowed chloramine level. In thirteenth embodiments, the controller is further configured to determine a time for replacement of said first filter module and to output an alarm signal indicating that said first filter module should be replaced, the time for replacement being determined based on a measured total volume and/or a total time since a last replacement of the first filter module and taking into account a predicted primary water quality.

Any of the foregoing thirteenth embodiments may be varied to form additional thirteenth embodiments in which the predefined level is more than 4 megohm-cm. Any of the foregoing thirteenth embodiments may be varied to form additional thirteenth embodiments in which the predefined level is more than 6 megohm-cm. Any of the foregoing thirteenth embodiments may be varied to form additional thirteenth embodiments in which the predefined level is more than 8 megohm-cm. Any of the foregoing thirteenth embodiments may be varied to form additional thirteenth embodiments in which the predefined level is at least 10 megohm-cm. Any of the foregoing thirteenth embodiments may be varied to form additional thirteenth embodiments in which the first filter module includes an activated carbon filter. Any of the foregoing thirteenth embodiments may be varied to form additional thirteenth embodiments in which the system further comprises a deionization filter upstream or downstream of the first filter module, wherein the first filter module includes an activated carbon filter. Any of the foregoing thirteenth embodiments may be varied to form additional thirteenth embodiments in which the first filter module includes an activated carbon filter and a deionization filter which are configured to be replaced as a modular unit. Any of the foregoing thirteenth embodiments may be varied to form additional thirteenth embodiments in which the system further comprises a medical treatment device adapted for receiving product water according to demand by the medical treatment device. Any of the foregoing thirteenth embodiments may be varied to form additional thirteenth embodiments in which the system further comprises a medical treatment device adapted for receiving product water according to demand by the medical treatment device, the medical treatment device including medicament preparation component adapted receive product water from the resistivity testing element and generate a medicament therefrom. Any of the foregoing thirteenth embodiments may be varied to form additional thirteenth embodiments in which the system further comprises a medical treatment device adapted for receiving product water according to demand by the medical treatment device, the medical treatment device including medicament preparation component and a medicament-consuming component that is adapted to deliver a medical treatment to a patient. Any of the foregoing thirteenth embodiments may be varied to form additional thirteenth embodiments in which the medical treatment device includes a dialysate preparation component. Any of the foregoing thirteenth embodiments may be varied to form additional thirteenth embodiments in which the dialysate preparation component includes a proportioning device adapted to mix medicament concentrate with product water by generating a mechanical or electronic command signal to convey product water. Any of the foregoing thirteenth embodiments may be varied to form additional thirteenth embodiments in which the resistivity testing element includes a temperature sensor and the resistivity testing element, the controller being adapted for controlling the fluid circuit responsively to a resistance signal generated by said resistivity testing element and a temperature signal generated by said temperature sensor. Any of the foregoing thirteenth embodiments may be varied to form additional thirteenth embodiments in which the resistivity testing element has a flow-through configuration adapted to detect resistivity continuously as fluid flows therethrough.

According to fourteenth embodiments thereof, a fluid processing system comprises a fluid circuit including a replaceable first filter module configured to remove chloramine from primary water and a resistivity testing element positioned downstream of the first filter module such that filtered water from the first filter module is tested thereby to detect for a threshold level of chloramine remaining in the filtered water. In fourteenth embodiments, the resistivity testing element is adapted to detect resistivity above 1 megohm-cm. In fourteenth embodiments, the system further comprises a medical treatment device adapted for receiving product water according to demand by the medical treatment device, the medical treatment device including medicament preparation component. In fourteenth embodiments, the first filter module, or a deionization filter upstream or downstream of the first filter module, is adapted to increase a resistivity of the filtered water received by the resistivity testing element, to a level higher than a predefined water quality requirement forming part of a medical treatment standard to which the medical treatment device is subject. In fourteenth embodiments, the system further comprises a controller configured to control a flow of water in the fluid circuit and to output an alarm signal. In fourteenth embodiments, the resistivity testing element is adapted to apply to the controller a resistivity signal indicating a resistivity of the filtered water received thereby and the controller being configured to control the flow of filtered water responsively to the resistivity signal such that said controller, in response to a resistivity above a predefined level of more 1 megohm-cm, or a rate of change of a resistivity above a predefined rate, causes said controller to output a signal indicating a water quality error. In fourteenth embodiments, the controller is further configured to determine a time for replacement of said first filter module and to output an alarm signal indicating that said first filter module should be replaced, the time for replacement being determined based on a measured total volume and/or a total time since a last replacement of the first filter module and taking into account a predicted primary water quality, so as to ensure that only a fraction less than 100% of a chloramine removal capacity of the first filter module has been consumed by said time for replacement.

Any of the foregoing fourteenth embodiments may be varied to form additional fourteenth embodiments in which the predefined level is more than 4 megohm-cm. Any of the foregoing fourteenth embodiments may be varied to form additional fourteenth embodiments in which the predefined level is more than 6 megohm-cm. Any of the foregoing fourteenth embodiments may be varied to form additional fourteenth embodiments in which the predefined level is more than 8 megohm-cm. Any of the foregoing fourteenth embodiments may be varied to form additional fourteenth embodiments in which the predefined level is at least 10 megohm-cm. Any of the foregoing fourteenth embodiments may be varied to form additional fourteenth embodiments in which the first filter module includes an activated carbon filter. Any of the foregoing fourteenth embodiments may be varied to form additional fourteenth embodiments in which the system further comprises a deionization filter upstream or downstream of the first filter module, wherein the first filter module includes an activated carbon filter. Any of the foregoing fourteenth embodiments may be varied to form additional fourteenth embodiments in which the first filter module includes an activated carbon filter and a deionization filter which are configured to be replaced as a modular unit. Any of the foregoing fourteenth embodiments may be varied to form additional fourteenth embodiments in which the medical treatment device includes medicament preparation component that is adapted receive product water from the resistivity testing element and generated a medicament therefrom. Any of the foregoing fourteenth embodiments may be varied to form additional fourteenth embodiments in which the system further comprises a medicament-consuming component that received medicament from the medicament preparation component and is adapted to deliver a medical treatment to a patient. Any of the foregoing fourteenth embodiments may be varied to form additional fourteenth embodiments in which the medicament preparation component includes a dialysate preparation component. Any of the foregoing fourteenth embodiments may be varied to form additional fourteenth embodiments in which the dialysate preparation component includes a proportioning device adapted to mix medicament concentrate with product water by generating a mechanical or electronic command signal to convey product water. Any of the foregoing fourteenth embodiments may be varied to form additional fourteenth embodiments in which the resistivity testing element includes a temperature sensor and the resistivity testing element, the controller being adapted for controlling said fluid circuit responsively to a resistance signal generated by said resistivity testing element and a temperature signal generated by said temperature sensor. Any of the foregoing fourteenth embodiments may be varied to form additional fourteenth embodiments in which the resistivity testing element has a flow-through configuration adapted to detect resistivity continuously as fluid flows therethrough. Any of the foregoing fourteenth embodiments may be varied to form additional fourteenth embodiments in which the fluid circuit includes at least one pump controlled by said controller responsively to said resistivity above a predefined level. Any of the foregoing fourteenth embodiments may be varied to form additional fourteenth embodiments in which the fluid circuit includes at least one pump controlled by said controller to halt said at least one pump responsively to said resistivity above a predefined level. Any of the foregoing fourteenth embodiments may be varied to form additional fourteenth embodiments in which the fluid circuit includes at least one pump controlled by said controller responsively to said resistivity above a predefined level. Any of the foregoing fourteenth embodiments may be varied to form additional fourteenth embodiments in which the fluid circuit includes at least one pump controlled by said controller to halt said at least one pump responsively to said resistivity above a predefined level. Any of the foregoing fourteenth embodiments may be varied to form additional fourteenth embodiments in which the fluid circuit includes at least one control valve controlled by said controller responsively to said resistivity above a predefined level. Any of the foregoing fourteenth embodiments may be varied to form additional fourteenth embodiments in which the fluid circuit includes at least one control valve controlled by said controller to halt or divert a flow of water using at least one control valve responsively to said resistivity above a predefined level. Any of the foregoing fourteenth embodiments may be varied to form additional fourteenth embodiments in which the fluid circuit includes at least one control valve controlled by said controller responsively to said resistivity above a predefined level. Any of the foregoing fourteenth embodiments may be varied to form additional fourteenth embodiments in which the fluid circuit includes at least one pump controlled by said controller to halt or divert a flow of water using said at least one control valve responsively to said resistivity above a predefined level. Any of the foregoing fourteenth embodiments may be varied to form additional fourteenth embodiments in which the system further comprises a second filter module configured to remove chloramine.

According to fifteenth embodiments thereof, a method of delivering a blood treatment comprises carbon-filtering primary tap water to generate substantially chloramine-free water and deionizing the substantially chloramine-free water to a predetermined level of resistivity, to generate deionized product water, the predetermined level being selected to be low enough to permit a detection of chloramine in the deionized product water resulting from a failure of said carbon-filtering. In fifteenth embodiments, the method further comprises using a controller determining that at least one carbon filter used to perform said carbon-filtering is to be replaced and, responsively to said determining, outputting an alarm signal to replace said at least one carbon filter. In fifteenth embodiments, the determining is effective to ensure that a chloramine level in said deionized product water is below a predetermine safe level for use in a dialysis, hemodiafiltration, or hemofiltration treatment of a human, said predefined safe level being according to a predefined medical standard with a margin for safety based on a predicted water quality and a predicted chloramine removing efficacy of said at least one carbon filter. In fifteenth embodiments, the method further comprises ensuring in the event an error in said carbon-filtering, that said deionized product water is safe, detecting chloramine in the deionized product water resulting from a failure of said carbon-filtering and controlling a flow of said deionized product water responsively thereto. In fifteenth embodiments the detecting includes converting a resistivity signal to a chloramine level based on data representing a relationship between chloramine level and resistivity stored in the controller.

Any of the foregoing fifteenth embodiments may be varied to form additional fifteenth embodiments in which the controlling a flow includes halting a flow of said deionized product water. Any of the foregoing fifteenth embodiments may be varied to form additional fifteenth embodiments in which the controlling a flow includes generating a command to halt a flow of said deionized product water. Any of the foregoing fifteenth embodiments may be varied to form additional fifteenth embodiments in which the controlling a flow includes generating a user interface output indicating an error in the level of chloramine in said deionized product water. Any of the foregoing fifteenth embodiments may be varied to form additional fifteenth embodiments in which the method further comprises supplying said deionized product water to a proportioning system to generate a medicament therefrom and making said medicament available for a blood treatment. Any of the foregoing fifteenth embodiments may be varied to form additional fifteenth embodiments in which the predetermined level of resistivity is determined responsively to a temperature of the deionized product water. Any of the foregoing fifteenth embodiments may be varied to form additional fifteenth embodiments in which the level of resistivity is at least 2.5 megohm-cm. Any of the foregoing fifteenth embodiments may be varied to form additional fifteenth embodiments in which the predefined level of resistivity is more than 4 megohm-cm. Any of the foregoing fifteenth embodiments may be varied to form additional fifteenth embodiments in which the predefined level of resistivity is more than 6 megohm-cm. Any of the foregoing fifteenth embodiments may be varied to form additional fifteenth embodiments in which the predefined level of resistivity is more than 8 megohm-cm. Any of the foregoing fifteenth embodiments may be varied to form additional fifteenth embodiments in which the predefined level of resistivity is at least 10 megohm-cm. Any of the foregoing fifteenth embodiments may be varied to form additional fifteenth embodiments in which the level of resistivity is at least 2.5 megohm-cm. Any of the foregoing fifteenth embodiments may be varied to form additional fifteenth embodiments in which the predefined level of resistivity is more than 4 megohm-cm. Any of the foregoing fifteenth embodiments may be varied to form additional fifteenth embodiments in which the predefined level of resistivity is more than 6 megohm-cm. Any of the foregoing fifteenth embodiments may be varied to form additional fifteenth embodiments in which the predefined level of resistivity is more than 8 megohm-cm. Any of the foregoing fifteenth embodiments may be varied to form additional fifteenth embodiments in which the predefined level of resistivity is at least 10 megohm-cm. Any of the foregoing fifteenth embodiments may be varied to form additional fifteenth embodiments in which the predefined level of resistivity is selected based on a minimum level required to reliably detect a presence of chloramine in said deionized product water.

According to sixteenth embodiments thereof, a method for purifying water produces a product water meeting a predefined water quality requirement that includes a predefined limit on the amount of a specific dissolved species that is weakly conductive and a lower limit on the allowed resistivity of said product water due to all dissolved species. In sixteenth embodiments, the method comprises removing the specific dissolved species from a primary water stream using a first filter to produce primary water depleted of the specific dissolved species, and using a second filter, filtering the primary water depleted of the specific dissolved species to reduce other dissolved species sufficient to produce high resistivity product water whose resistivity is sufficiently high to permit the detection of the specific dissolved species using a resistivity detector. In sixteenth embodiments, the method further comprises using a controller, predicting, based on a parameter that is responsive to time of use of the first filter, and outputting from the controller, a first signal indicating a requirement to replace the first filter, the predicting being such that there is a sufficient remaining capacity to remove the specific dissolved species from the primary water stream to ensure that said product water meets said predefined limit on the amount of a specific dissolved species under non-error conditions. In sixteenth embodiments, the method further comprises using the controller, monitoring the resistivity of the high resistivity product water and generating a second signal indicating the detection of a product water quality error responsively to said monitoring, whereby, in the event of a failure of the predicting adequately to ensure that said product water meets said predefined limit on the amount of a specific dissolved species.

Any of the foregoing sixteenth embodiments may be varied to form additional sixteenth embodiments in which the monitoring includes converting a resistivity measurement of said product water to a level of said specific dissolved species based on data representing the relationship between the level of the specific dissolved species and the resistivity. Any of the foregoing sixteenth embodiments may be varied to form additional sixteenth embodiments in which the filtering the primary water depleted of the specific dissolved species includes deionizing the primary water depleted of the specific dissolved species in a first deionization filter, monitoring the resistivity of water derived from the first deionization filter to detect exhaustion of the first deionization filter, and filtering the water from the first deionization filter with a backup deionization filter. Any of the foregoing sixteenth embodiments may be varied to form additional sixteenth embodiments in which the non-error conditions include a range of primary water quality. Any of the foregoing sixteenth embodiments may be varied to form additional sixteenth embodiments in which the first filter includes a filter that removes the specific dissolved species using an adsorbent and the second filter uses a chemical reaction to remove ions from the primary water depleted of the specific dissolved species. Any of the foregoing sixteenth embodiments may be varied to form additional sixteenth embodiments in which the first filter includes activated carbon. Any of the foregoing sixteenth embodiments may be varied to form additional sixteenth embodiments in which the controller is a programmable controller with a flow sensor that performs said predicting responsively to a signal from the said flow sensor and such that said predicting is responsive to a cumulative historical flow since the first filter was replaced. Any of the foregoing sixteenth embodiments may be varied to form additional sixteenth embodiments in which the controller is a programmable controller, with a timer, that performs said predicting responsively to said timer and such that said predicting is responsive to a cumulative time since the first filter was replaced. Any of the foregoing sixteenth embodiments may be varied to form additional sixteenth embodiments in which the controller is a programmable controller, with a timer, that performs said predicting responsively to said timer and such that said predicting is responsive to a cumulative time since the first filter was replaced. Any of the foregoing sixteenth embodiments may be varied to form additional sixteenth embodiments in which said second filter includes a deionization filter. Any of the foregoing sixteenth embodiments may be varied to form additional sixteenth embodiments in which the product water is generated at a treatment site and said method further includes generating a medicament for use in performing a blood treatment. Any of the foregoing sixteenth embodiments may be varied to form additional sixteenth embodiments in which the specific dissolved species includes chlorine or compounds thereof. Any of the foregoing sixteenth embodiments may be varied to form additional sixteenth embodiments in which the product water is generated at a treatment site and said method further includes generating a medicament and made available for use in performing a blood treatment. Any of the foregoing sixteenth embodiments may be varied to form additional sixteenth embodiments in which the method does not include routine chemical testing for said specific dissolved species.

According to seventeenth embodiments thereof, a fluid processing system is adapted for providing purified water for a use requiring water to have a resistivity of no more than a use level which is substantially below 2.5 megohm-cm. In seventeenth embodiments, the system comprises a fluid circuit including a replaceable first filter module configured to remove chloramine from primary water and a resistivity testing element positioned downstream of the first filter module such that filtered water from the first filter module is tested thereby to detect for a threshold level of chloramine remaining in the filtered water. In seventeenth embodiments, the resistivity testing element is adapted to indicate resistivity above 2.5 megohm-cm, and the first filter module, or a deionization filter upstream or downstream of the first filter module, is adapted to filter water so as to achieve a resistivity of the water filtered thereby and received by the resistivity testing element, to a level higher than 2.5 megohm-cm. In seventeenth embodiments, the system further comprises a controller connected to the resistivity testing element, configured to control a flow of water in the fluid circuit, and to output an alarm signal. In seventeenth embodiments, the resistivity testing element is connected to apply to the controller a resistivity signal indicating a resistivity of the filtered water received thereby and the controller being configured to control the flow of filtered water responsively to the resistivity signal such that said controller, in response to a resistivity above a predefined level of at least 2.5 megohm-cm, or a rate of change of a resistivity above a predefined rate, causes said controller to output a signal indicating a water quality error. In seventeenth embodiments the controller is further configured to determine a time for replacement of said first filter module and to output an alarm signal indicating that said first filter module should be replaced, the time for replacement being determined based on a measured total volume and/or a total time since a last replacement of the first filter module and taking into account a predicted primary water quality, to ensure that only a fraction less than 100% of a chloramine removal capacity of the first filter module has been consumed by said time for replacement.

Any of the foregoing seventeenth embodiments may be varied to form additional seventeenth embodiments in which the predefined level is more than 4 megohm-cm. Any of the foregoing seventeenth embodiments may be varied to form additional seventeenth embodiments in which the predefined level is more than 6 megohm-cm. Any of the foregoing seventeenth embodiments may be varied to form additional seventeenth embodiments in which the predefined level is more than 8 megohm-cm. Any of the foregoing seventeenth embodiments may be varied to form additional seventeenth embodiments in which the predefined level is at least 10 megohm-cm. Any of the foregoing seventeenth embodiments may be varied to form additional seventeenth embodiments in which the first filter module includes an activated carbon filter. Any of the foregoing seventeenth embodiments may be varied to form additional seventeenth embodiments in which the system further comprises a deionization filter upstream or downstream of the first filter module, wherein the first filter module includes an activated carbon filter. Any of the foregoing seventeenth embodiments may be varied to form additional seventeenth embodiments in which the first filter module includes an activated carbon filter and a deionization filter which are configured to be replaced as a modular unit. Any of the foregoing seventeenth embodiments may be varied to form additional seventeenth embodiments in which the system further comprises a medical treatment device adapted for receiving product water according to demand by the medical treatment device. Any of the foregoing seventeenth embodiments may be varied to form additional seventeenth embodiments in which the system further comprises a medical treatment device adapted for receiving product water according to demand by the medical treatment device, the medical treatment device including medicament preparation component adapted receive product water from the resistivity testing element and generate a medicament therefrom. Any of the foregoing seventeenth embodiments may be varied to form additional seventeenth embodiments in which the system further comprises a medical treatment device adapted for receiving product water according to demand by the medical treatment device, the medical treatment device including medicament preparation component and a medicament-consuming component that is adapted to deliver a medical treatment to a patient. Any of the foregoing seventeenth embodiments may be varied to form additional seventeenth embodiments in which the medical treatment device includes a dialysate preparation component. Any of the foregoing seventeenth embodiments may be varied to form additional seventeenth embodiments in which the dialysate preparation component includes a proportioning device adapted to mix medicament concentrate with product water by generating a mechanical or electronic command signal to convey product water. Any of the foregoing seventeenth embodiments may be varied to form additional seventeenth embodiments in which the resistivity testing element includes a temperature sensor and the resistivity testing element, the controller being adapted for controlling the fluid circuit responsively to a resistance signal generated by said resistivity testing element and a temperature signal generated by said temperature sensor. Any of the foregoing seventeenth embodiments may be varied to form additional seventeenth embodiments in which the resistivity testing element has a flow-through configuration adapted to detect resistivity continuously as fluid flows therethrough.

It will be appreciated that the modules, processes, systems, and sections described above can be implemented in hardware, hardware programmed by software, software instruction stored on a non-transitory computer readable medium or a combination of the above. For example, a method for preparing purified water, a medicament based on purified water, a method for detecting chloramine, a method for controlling a water treatment system, or a method for controlling a blood treatment system, can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of programmable controllers and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, devices, methods, and system for purifying water, preparing treatment fluids, performing blood treatments, and various other embodiments. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

The invention claimed is:

1. A method of delivering a blood treatment, comprising:
carbon-filtering primary tap water to generate chloramine-free water;
deionizing the chloramine-free water to a predetermined level of resistivity, to generate deionized product water, the predetermined level of resistivity being selected to be low enough to permit a detection of chloramine in the deionized product water resulting from a failure of said carbon-filtering;
determining, responsively to time and/or to a cumulative volume of the chloramine-free water generated by said carbon-filtering, that at least one carbon filter used to perform said carbon-filtering is to be replaced and, responsively to said determining, outputting a command signal to replace said at least one carbon filter;
said determining being effective to ensure that a chloramine level in said deionized product water is below a predetermined safe level for use in a dialysis, hemodiafiltration, or hemofiltration treatment of a human, said predetermined safe level being according to a predefined medical standard with a margin for safety based on a predicted water quality and a predicted chloramine removing efficacy of said at least one carbon filter; and
ensuring in case of an error in said carbon-filtering, that said deionized product water is safe, by determining a chloramine concentration in the deionized product water based on a resistivity measurement and a temperature measurement of the deionized product water; and
controlling a flow of said deionized product water responsively to the determining.

2. The method of claim 1, wherein the controlling the flow includes generating a command to halt the flow of said deionized product water.

3. The method of claim 1, wherein the controlling the flow includes generating a user interface output indicating an error in a level of chloramine in said deionized product water.

4. The method of claim 1, further comprising supplying said deionized product water to a proportioning system to generate a medicament therefrom and making said medicament available for the blood treatment.

5. The method of claim 4, wherein the predetermined level of resistivity is determined responsively to a temperature of the deionized product water.

6. The method of claim 4, wherein the predetermined level of resistivity is at least 2.5 megohm-cm.

7. A method for purifying water to produce a product water meeting a predefined water quality requirement that includes a predefined limit on an amount of chloramine and a lower limit on an allowed resistivity of said product water due to all dissolved species, the method comprising:

removing the chloramine from a stream of primary water using a first filter to produce primary water depleted of the chloramine;

using a second filter, filtering the primary water depleted of the chloramine to reduce other dissolved species sufficient to produce high resistivity product water whose resistivity is sufficiently high to permit detection of the chloramine using a resistivity detector;

using a controller, predicting, based on a parameter that is responsive to time of use of the first filter, and outputting from the controller, a first signal indicating a requirement to replace the first filter, the predicting being such that there is a sufficient remaining capacity to remove the chloramine from the stream of the primary water to ensure that said product water meets said predefined limit on the amount of the chloramine under non-error conditions;

using the controller, monitoring the resistivity of the high resistivity product water and determining a chloramine concentration in the high resistivity product water from the resistivity and a temperature measurement; and generating a second signal indicating a product water quality error responsively to determining that the chloramine concentration exceeds the predefined limit.

8. The method of claim 7, wherein the non-error conditions include a range of primary water quality.

9. The method of claim 7, wherein the first filter includes a filter element that removes the chloramine using an adsorbent and the second filter uses a chemical reaction to remove ions from the primary water depleted of the chloramine.

10. The method of claim 7, wherein the controller is a programmable controller with a flow sensor that performs said predicting responsively to a signal from the said flow sensor and such that said predicting is responsive to a cumulative historical flow since the first filter was replaced.

11. The method of claim 7, wherein the controller is a programmable controller, with a timer, that performs said predicting responsively to said timer and such that said predicting is responsive to a cumulative time since the first filter was replaced.

12. The method of claim 7, wherein the product water is generated at a treatment site and said method further includes generating a medicament for use in performing a blood treatment.

13. The method of claim 12, wherein the method does not include routine chemical testing for said chloramine.

* * * * *